United States Patent
Wang et al.

(10) Patent No.: US 9,975,962 B2
(45) Date of Patent: May 22, 2018

(54) THROMBIN/PLASMIN-REGULATED ANTIBODIES THAT BIND TFPI

(71) Applicant: Bayer HealthCare LLC, Whippany, NJ (US)

(72) Inventors: Zhuozhi Wang, Millbrae, CA (US); Ruth Winter, Oakland, CA (US); John Murphy, Berkeley, CA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 54 days.

(21) Appl. No.: 14/389,219

(22) PCT Filed: Mar. 14, 2013

(86) PCT No.: PCT/US2013/031363
§ 371 (c)(1),
(2) Date: Sep. 29, 2014

(87) PCT Pub. No.: WO2013/148248
PCT Pub. Date: Oct. 3, 2013

(65) Prior Publication Data
US 2015/0064169 A1 Mar. 5, 2015

Related U.S. Application Data

(60) Provisional application No. 61/617,837, filed on Mar. 30, 2012.

(51) Int. Cl.
*C07K 16/36* (2006.01)
*C07K 14/745* (2006.01)
*C07K 16/38* (2006.01)
*A61K 39/395* (2006.01)

(52) U.S. Cl.
CPC ............ *C07K 16/38* (2013.01); *C07K 14/745* (2013.01); *C07K 16/36* (2013.01); *A61K 39/3955* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 5,179,017 A | 1/1993 | Axel et al. |
| 2003/0109000 A1 | 6/2003 | Moore et al. |
| 2011/0229476 A1 | 9/2011 | Liu et al. |

FOREIGN PATENT DOCUMENTS

| | | |
|---|---|---|
| WO | 9945962 A1 | 9/1999 |
| WO | 2009067800 A1 | 6/2009 |
| WO | 2010017196 A2 | 2/2010 |
| WO | 2011109452 A1 | 9/2011 |
| WO | 2012001087 A1 | 1/2012 |
| WO | 2012135671 A2 | 10/2012 |
| WO | 2013148248 A1 | 10/2013 |

OTHER PUBLICATIONS

International Search Report and Written Opinion for PCT/US2013/031363, mailed Jul. 24, 2013.
Zhang, et al. A polyclonal anti-vaccine CD4 T cell response detected with HLA-DP4 multimers in a melanoma patient vaccinated with MAGE-3.DP4-peptide-pulsed dendritic cells. Eur. J. Immunol. 2005, 35:1006-1075.
Bajaj; et al., "Structure and Biology of Tissue Factor Pathway Inhibitor", 2001, vol. 86, 959-972.
Bird; et al., "Single-Chain Antigen-Binding Proteins", Oct. 21, 1988, vol. 242 No. 4877, 423-426.
Brekke; et al., "Therapeutic Antibodies for Human Diseases at the Dawm of the Twenty-First Century", Jan. 2003, vol. 2 No. 53, 52-62.
Briggs; Peter, "Comparison of SURFACE and AREAIMOL", Apr. 2000, No. 38, 7-13.
Burgering; J.M. et al., "The Second Kunitz Domain of Human Tissue Factor Pathway Inhibitor: Cloning, Structure Determination and Interaction with Factor Xa", Jun. 13, 1997, vol. 269 No. 3, 395-407.
Emsley; et al., "Features and Development of Coot", 2010, D66, 486-501.
Erhardtsen; et al., "Blocking of Tissue Factor Pathway Inhibitor (TFPI) Shortens the Bleeding Time in Rabbits with Antibody Induced Haemophilia A", Jul. 1995, vol. 6 No. 5, 388-394.
Evans; Philip, "Scaling and Assessment of Data Quality", 2006, D62, 72-82.
Fiser; et al., "Modeller: Generation and Refinement of Homology-Based Protein Structure Models", vol. 374, 461-491.
Goeddel; David V., "Systems for Heterologous Gene Expression", 1990, vol. 185, 3-7.
Higgins; et al., "Clustal V: Improved Software for Multiple Sequence Alignment", 1992, vol. 8 No. 2, 189-191.
Huston; et al., "Protein Engineering of Antibody Binding Sites: Recovery of Specific Activity in an Anti-Digoxin Single-Chain Fv Analogue Produced in *Escherichia coli*", Aug. 1988, vol. 85 No. 16, 5879-5883.
Ill; et al., "Design and Construction of a Hybrid Immunoglobulin Domain with Properties of Both Heavy and Light Chain Variable Regions", Aug. 1, 1997, vol. 10 No. 8, 949-957.
Jones; Peter T., "Replacing the Complementarity-Determining Regions in a Human Antibody with those from a Mouse", May 1986, vol. 321, 522-525.
Kaufman; et al., "Amplification and Expression of Sequences Cotransfected with a Modular Dihydrofolate Reductase Complementary DNA Gene", 1982, vol. 159, 601-621.
Kohler; et al., "Continuous Cultures of Fused Cells Secreting Antibody of Predefined Specificity", Aug. 7, 1975, vol. 256, 495-497.

(Continued)

*Primary Examiner* — Zachary Howard
(74) *Attorney, Agent, or Firm* — Timothy H. Joyce

(57) ABSTRACT

This disclosure provides protease-regulated antibodies which specifically bind to tissue factor pathway inhibitor (TFPI). The antibodies are useful for treating bleeding disorders such as hemophilia.

1 Claim, 9 Drawing Sheets

(56) References Cited

OTHER PUBLICATIONS

Kozak; Marilyn, "Structural Features in Eukaryotic mRNAs That Modulate the Initiation of Translation", Oct. 25, 1991, vol. 266 No. 30, 19867-19870.
Leslie; A.G.W., "Recent changes to the MOSFLM package for processing film and image plate data", Apr. 1992, No. 26, 29-35.
McCoy; et al., "Phaser Crystallographic Software", Apr. 27, 2007, vol. 40, 658-674.
Murshudov; et al., "REFMAC5 for the Refinement of Macromolecular Crystal Structures", Jan. 10, 2011, D67, 355-367.
Nordfang; et al., "Inhibition of Extrinsic Pathway Inhibitor Shortens the Coagulation Time of Normal Plasma and of Hemophilia Plasma", Oct. 1, 1991, vol. 66 No. 4, 464-467.
Queen et al., A Humanized Antibody that Binds to the Interleukin 2 Receptor, Proceedings of the National Academy of Sciences of the United States of America, Dec. 1989, 10029-10033, vol. 86.
Riechmann et al.,Reshaping Human Antibodies for Therapy, Nature, Mar. 24, 1988, 323-327, vol. 332.
Stein; Norman, "CHAINSAW: A Program for Mutating PDB Files used as Templates in Molecular Replacement", 2008, vol. 41, 641-643.
"The CCP4 Suite: Programs for Protein Crystallography", Mar. 21, 1994, D50, 760-763.
Thompson; et al., "CLUSTAL W: Improving the Sensitivity of Progressive Multiple Sequence Alignment Through Sequence Weighting, Position-Specific Gap Penalties and Weight Matrix Choice", 1994, vol. 22, No. 22, 4673-4680.
Urlaub; et al., "Isolation of Chinese Hamster Cell Mutants Deficient in Dihydrofolate Reductase Activity", Jul. 1980, vol. 77 No. 7, 4216-4220.
Ward; et al., "Binding activities of a repertoire of single immunoglobulin variable domains secreted from *Escherichia coli*", Oct. 12, 1989, vol. 341, 544-546.
Yang; et al., "Effect of Monoclonal Antibody Against Human Tissue Factor Pathway Inhibitor on Plasma Coagulation Time", 1997, vol. 22 No. 4, 297-300.
Zhang; et al., "Structure of Extracellular Tissue Factor Complexed with Factor Vila Inhibited with a BPTI Mutant", 1999, vol. 285, 1089-2104.

SEQUENCE LISTING

```
<160> NUMBER OF SEQ ID NOS: 180

<210> SEQ ID NO 1
<211> LENGTH: 8
<212> TYPE: PRT
<213> ORGANISM: Artificial Sequence
<220> FEATURE:
<223> OTHER INFORMATION: protease cleavage site

<400> SEQUENCE: 1

Ala His Pro Arg Ile Ile Ser Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: protease cleavage site

<400> SEQUENCE: 2

Ala Arg Thr Arg Ala Arg Arg Pro
 1               5

<210> SEQ ID NO 3
<211> LENGTH: 8
<212> TYPE: PRT
<213> ORGANISM: Artificial Sequence
<220> FEATURE:
<223> OTHER INFORMATION: protease cleavage site

<400> SEQUENCE: 3

Ala Ser Ala Arg Thr Thr Gly Ser
 1               5

<210> SEQ ID NO 4
<211> LENGTH: 8
<212> TYPE: PRT
<213> ORGANISM: Artificial Sequence
<220> FEATURE:
<223> OTHER INFORMATION: protease cleavage site

<400> SEQUENCE: 4

Ala Thr Pro Arg Gly Ala Ala Pro
 1               5

<210> SEQ ID NO 5
<211> LENGTH: 8
<212> TYPE: PRT
<213> ORGANISM: Artificial Sequence
<220> FEATURE:
<223> OTHER INFORMATION: protease cleavage site

<400> SEQUENCE: 5

Ala Val Val Arg Thr Pro Pro Lys
 1               5

<210> SEQ ID NO 6
<211> LENGTH: 8
<212> TYPE: PRT
```

<213> ORGANISM: Artificial Sequence
<220> FEATURE:
<223> OTHER INFORMATION: protease cleavage site

<400> SEQUENCE: 6

Glu Arg Thr Arg Ser Phe Gln Leu
 1               5

<210> SEQ ID NO 7
<211> LENGTH: 8
<212> TYPE: PRT
<213> ORGANISM: Artificial Sequence
<220> FEATURE:
<223> OTHER INFORMATION: protease cleavage site

<400> SEQUENCE: 7

Phe Gly Leu Arg Phe Tyr Ala Tyr
 1               5

<210> SEQ ID NO 8
<211> LENGTH: 8
<212> TYPE: PRT
<213> ORGANISM: Artificial Sequence
<220> FEATURE:
<223> OTHER INFORMATION: protease cleavage site

<400> SEQUENCE: 8

Phe Asn Pro Arg Thr Phe Gly Ser
 1               5

<210> SEQ ID NO 9
<211> LENGTH: 8
<212> TYPE: PRT
<213> ORGANISM: Artificial Sequence
<220> FEATURE:
<223> OTHER INFORMATION: protease cleavage site

<400> SEQUENCE: 9

Phe Arg Pro Lys His Thr Arg Ile
 1               5

<210> SEQ ID NO 10
<211> LENGTH: 8
<212> TYPE: PRT
<213> ORGANISM: Artificial Sequence
<220> FEATURE:
<223> OTHER INFORMATION: protease cleavage site

<400> SEQUENCE: 10

Phe Ser Ala Arg Gly His Arg Pro
 1               5

<210> SEQ ID NO 11
<211> LENGTH: 8
<212> TYPE: PRT
<213> ORGANISM: Artificial Sequence
<220> FEATURE:
<223> OTHER INFORMATION: protease cleavage site

<400> SEQUENCE: 11

Gly Asp Ile Arg Gly Pro Arg Ile
 1               5

<210> SEQ ID NO 12
<211> LENGTH: 8
<212> TYPE: PRT
<213> ORGANISM: Artificial Sequence

```
<220> FEATURE:
<223> OTHER INFORMATION: protease cleavage site

<400> SEQUENCE: 12

Gly Gly Val Arg Gly Pro Arg Val
 1               5

<210> SEQ ID NO 13
<211> LENGTH: 8
<212> TYPE: PRT
<213> ORGANISM: Artificial Sequence
<220> FEATURE:
<223> OTHER INFORMATION: protease cleavage site

<400> SEQUENCE: 13

Gly Ser Phe Arg Ala Gly Leu Phe
 1               5

<210> SEQ ID NO 14
<211> LENGTH: 8
<212> TYPE: PRT
<213> ORGANISM: Artificial Sequence
<220> FEATURE:
<223> OTHER INFORMATION: protease cleavage site

<400> SEQUENCE: 14

His Lys Gly Arg Ser Ala Leu Val
 1               5

<210> SEQ ID NO 15
<211> LENGTH: 8
<212> TYPE: PRT
<213> ORGANISM: Artificial Sequence
<220> FEATURE:
<223> OTHER INFORMATION: protease cleavage site

<400> SEQUENCE: 15

Ile Ala Gly Arg Ser Leu Asn Pro
 1               5

<210> SEQ ID NO 16
<211> LENGTH: 8
<212> TYPE: PRT
<213> ORGANISM: Artificial Sequence
<220> FEATURE:
<223> OTHER INFORMATION: protease cleavage site

<400> SEQUENCE: 16

Ile Asp Gly Arg Ile Val Glu Gly
 1               5

<210> SEQ ID NO 17
<211> LENGTH: 8
<212> TYPE: PRT
<213> ORGANISM: Artificial Sequence
<220> FEATURE:
<223> OTHER INFORMATION: protease cleavage site

<400> SEQUENCE: 17

Ile Glu Pro Arg Ser Phe Ser Gln
 1               5

<210> SEQ ID NO 18
<211> LENGTH: 8
<212> TYPE: PRT
<213> ORGANISM: Artificial Sequence
<220> FEATURE:
```

-continued

```
<223> OTHER INFORMATION: protease cleavage site

<400> SEQUENCE: 18

Ile Lys Pro Arg Ile Val Gly Gly
1               5

<210> SEQ ID NO 19
<211> LENGTH: 8
<212> TYPE: PRT
<213> ORGANISM: Artificial Sequence
<220> FEATURE:
<223> OTHER INFORMATION: protease cleavage site

<400> SEQUENCE: 19

Ile Gln Ile Arg Ser Val Ala Lys
1               5

<210> SEQ ID NO 20
<211> LENGTH: 8
<212> TYPE: PRT
<213> ORGANISM: Artificial Sequence
<220> FEATURE:
<223> OTHER INFORMATION: protease cleavage site

<400> SEQUENCE: 20

Ile Gln Ile Arg Ser Val Ala Lys
1               5

<210> SEQ ID NO 21
<211> LENGTH: 8
<212> TYPE: PRT
<213> ORGANISM: Artificial Sequence
<220> FEATURE:
<223> OTHER INFORMATION: protease cleavage site

<400> SEQUENCE: 21

Lys Asn Val Lys Ser Lys Ile Gly
1               5

<210> SEQ ID NO 22
<211> LENGTH: 8
<212> TYPE: PRT
<213> ORGANISM: Artificial Sequence
<220> FEATURE:
<223> OTHER INFORMATION: protease cleavage site

<400> SEQUENCE: 22

Lys Pro Lys Asp Ser Ser Val Asp
1               5

<210> SEQ ID NO 23
<211> LENGTH: 8
<212> TYPE: PRT
<213> ORGANISM: Artificial Sequence
<220> FEATURE:
<223> OTHER INFORMATION: protease cleavage site

<400> SEQUENCE: 23

Leu Asp Pro Arg Ser Phe Leu Leu
1               5

<210> SEQ ID NO 24
<211> LENGTH: 8
<212> TYPE: PRT
<213> ORGANISM: Artificial Sequence
<220> FEATURE:
<223> OTHER INFORMATION: protease cleavage site
```

```
<400> SEQUENCE: 24

Leu Gly Ile Arg Ser Phe Arg Asn
 1               5

<210> SEQ ID NO 25
<211> LENGTH: 8
<212> TYPE: PRT
<213> ORGANISM: Artificial Sequence
<220> FEATURE:
<223> OTHER INFORMATION: protease cleavage site

<400> SEQUENCE: 25

Leu Pro Ile Lys Thr Phe Arg Gly
 1               5

<210> SEQ ID NO 26
<211> LENGTH: 8
<212> TYPE: PRT
<213> ORGANISM: Artificial Sequence
<220> FEATURE:
<223> OTHER INFORMATION: protease cleavage site

<400> SEQUENCE: 26

Leu Arg Pro Arg Phe Lys Ile Ile
 1               5

<210> SEQ ID NO 27
<211> LENGTH: 8
<212> TYPE: PRT
<213> ORGANISM: Artificial Sequence
<220> FEATURE:
<223> OTHER INFORMATION: protease cleavage site

<400> SEQUENCE: 27

Leu Arg Pro Arg Ile Ile Gly Gly
 1               5

<210> SEQ ID NO 28
<211> LENGTH: 8
<212> TYPE: PRT
<213> ORGANISM: Artificial Sequence
<220> FEATURE:
<223> OTHER INFORMATION: protease cleavage site

<400> SEQUENCE: 28

Leu Ser Pro Arg Gly Val His Ile
 1               5

<210> SEQ ID NO 29
<211> LENGTH: 8
<212> TYPE: PRT
<213> ORGANISM: Artificial Sequence
<220> FEATURE:
<223> OTHER INFORMATION: protease cleavage site

<400> SEQUENCE: 29

Leu Ser Pro Arg Thr Phe His Pro
 1               5

<210> SEQ ID NO 30
<211> LENGTH: 8
<212> TYPE: PRT
<213> ORGANISM: Artificial Sequence
<220> FEATURE:
<223> OTHER INFORMATION: protease cleavage site
```

```
<400> SEQUENCE: 30

Met Thr Pro Arg Ser Glu Gly Ser
1               5

<210> SEQ ID NO 31
<211> LENGTH: 8
<212> TYPE: PRT
<213> ORGANISM: Artificial Sequence
<220> FEATURE:
<223> OTHER INFORMATION: protease cleavage site

<400> SEQUENCE: 31

Met Thr Pro Arg Ser Gly Gly Ser
1               5

<210> SEQ ID NO 32
<211> LENGTH: 8
<212> TYPE: PRT
<213> ORGANISM: Artificial Sequence
<220> FEATURE:
<223> OTHER INFORMATION: protease cleavage site

<400> SEQUENCE: 32

Met Thr Pro Arg Ser Arg Gly Ser
1               5

<210> SEQ ID NO 33
<211> LENGTH: 8
<212> TYPE: PRT
<213> ORGANISM: Artificial Sequence
<220> FEATURE:
<223> OTHER INFORMATION: protease cleavage site

<400> SEQUENCE: 33

Met Val Pro Arg Ala Val Tyr Leu
1               5

<210> SEQ ID NO 34
<211> LENGTH: 8
<212> TYPE: PRT
<213> ORGANISM: Artificial Sequence
<220> FEATURE:
<223> OTHER INFORMATION: protease cleavage site

<400> SEQUENCE: 34

Asn Val Pro Arg Ile Leu Ser Pro
1               5

<210> SEQ ID NO 35
<211> LENGTH: 8
<212> TYPE: PRT
<213> ORGANISM: Artificial Sequence
<220> FEATURE:
<223> OTHER INFORMATION: protease cleavage site

<400> SEQUENCE: 35

Pro Ala Pro Arg Gly Tyr Pro Gly
1               5

<210> SEQ ID NO 36
<211> LENGTH: 8
<212> TYPE: PRT
<213> ORGANISM: Artificial Sequence
<220> FEATURE:
<223> OTHER INFORMATION: protease cleavage site

<400> SEQUENCE: 36
```

```
Pro Asp Leu Arg Ser Cys Val Asn
 1               5

<210> SEQ ID NO 37
<211> LENGTH: 8
<212> TYPE: PRT
<213> ORGANISM: Artificial Sequence
<220> FEATURE:
<223> OTHER INFORMATION: protease cleavage site

<400> SEQUENCE: 37

Pro Gly Pro Arg Gly Pro Pro Pro
 1               5

<210> SEQ ID NO 38
<211> LENGTH: 8
<212> TYPE: PRT
<213> ORGANISM: Artificial Sequence
<220> FEATURE:
<223> OTHER INFORMATION: protease cleavage site

<400> SEQUENCE: 38

Pro Gly Ser Arg Ser Arg Thr Pro
 1               5

<210> SEQ ID NO 39
<211> LENGTH: 8
<212> TYPE: PRT
<213> ORGANISM: Artificial Sequence
<220> FEATURE:
<223> OTHER INFORMATION: protease cleavage site

<400> SEQUENCE: 39

Pro Gln Gly Arg Ile Val Gly Gly
 1               5

<210> SEQ ID NO 40
<211> LENGTH: 8
<212> TYPE: PRT
<213> ORGANISM: Artificial Sequence
<220> FEATURE:
<223> OTHER INFORMATION: protease cleavage site

<400> SEQUENCE: 40

Pro Gln Gly Arg Thr Thr Ala His
 1               5

<210> SEQ ID NO 41
<211> LENGTH: 8
<212> TYPE: PRT
<213> ORGANISM: Artificial Sequence
<220> FEATURE:
<223> OTHER INFORMATION: protease cleavage site

<400> SEQUENCE: 41

Pro Arg Ser Phe Leu Leu Arg Asn
 1               5

<210> SEQ ID NO 42
<211> LENGTH: 8
<212> TYPE: PRT
<213> ORGANISM: Artificial Sequence
<220> FEATURE:
<223> OTHER INFORMATION: protease cleavage site

<400> SEQUENCE: 42
```

```
Gln Ser Pro Arg Ser Phe Gln Lys
  1               5

<210> SEQ ID NO 43
<211> LENGTH: 8
<212> TYPE: PRT
<213> ORGANISM: Artificial Sequence
<220> FEATURE:
<223> OTHER INFORMATION: protease cleavage site

<400> SEQUENCE: 43

Gln Ser Pro Arg Ser Phe Gln Lys
  1               5

<210> SEQ ID NO 44
<211> LENGTH: 8
<212> TYPE: PRT
<213> ORGANISM: Artificial Sequence
<220> FEATURE:
<223> OTHER INFORMATION: protease cleavage site

<400> SEQUENCE: 44

Gln Tyr Leu Arg Val Pro Leu Val
  1               5

<210> SEQ ID NO 45
<211> LENGTH: 8
<212> TYPE: PRT
<213> ORGANISM: Artificial Sequence
<220> FEATURE:
<223> OTHER INFORMATION: protease cleavage site

<400> SEQUENCE: 45

Ser Glu Phe Arg Cys Leu Thr Pro
  1               5

<210> SEQ ID NO 46
<211> LENGTH: 8
<212> TYPE: PRT
<213> ORGANISM: Artificial Sequence
<220> FEATURE:
<223> OTHER INFORMATION: protease cleavage site

<400> SEQUENCE: 46

Ser Ile Gly Arg Ala Ser Leu His
  1               5

<210> SEQ ID NO 47
<211> LENGTH: 8
<212> TYPE: PRT
<213> ORGANISM: Artificial Sequence
<220> FEATURE:
<223> OTHER INFORMATION: protease cleavage site

<400> SEQUENCE: 47

Ser Lys Gly Arg Ser Leu Ile Gly
  1               5

<210> SEQ ID NO 48
<211> LENGTH: 8
<212> TYPE: PRT
<213> ORGANISM: Artificial Sequence
<220> FEATURE:
<223> OTHER INFORMATION: protease cleavage site

<400> SEQUENCE: 48

Ser Arg Leu Arg Ala Tyr Leu Leu
```

```
                    1               5

<210> SEQ ID NO 49
<211> LENGTH: 8
<212> TYPE: PRT
<213> ORGANISM: Artificial Sequence
<220> FEATURE:
<223> OTHER INFORMATION: protease cleavage site

<400> SEQUENCE: 49

Thr Cys Leu Arg Ser Thr Lys Phe
 1               5

<210> SEQ ID NO 50
<211> LENGTH: 8
<212> TYPE: PRT
<213> ORGANISM: Artificial Sequence
<220> FEATURE:
<223> OTHER INFORMATION: protease cleavage site

<400> SEQUENCE: 50

Val Cys Leu Arg Ser Phe Gln Thr
 1               5

<210> SEQ ID NO 51
<211> LENGTH: 8
<212> TYPE: PRT
<213> ORGANISM: Artificial Sequence
<220> FEATURE:
<223> OTHER INFORMATION: protease cleavage site

<400> SEQUENCE: 51

Val Asp Pro Arg Leu Ile Asp Gly
 1               5

<210> SEQ ID NO 52
<211> LENGTH: 8
<212> TYPE: PRT
<213> ORGANISM: Artificial Sequence
<220> FEATURE:
<223> OTHER INFORMATION: protease cleavage site

<400> SEQUENCE: 52

Val Glu Val Lys Ser Glu Lys Leu
 1               5

<210> SEQ ID NO 53
<211> LENGTH: 8
<212> TYPE: PRT
<213> ORGANISM: Artificial Sequence
<220> FEATURE:
<223> OTHER INFORMATION: protease cleavage site

<400> SEQUENCE: 53

Val Ile Pro Lys Arg Ile Ser Pro
 1               5

<210> SEQ ID NO 54
<211> LENGTH: 8
<212> TYPE: PRT
<213> ORGANISM: Artificial Sequence
<220> FEATURE:
<223> OTHER INFORMATION: protease cleavage site

<400> SEQUENCE: 54

Val Ile Pro Arg Ser Gly Gly Ser
 1               5
```

<210> SEQ ID NO 55
<211> LENGTH: 8
<212> TYPE: PRT
<213> ORGANISM: Artificial Sequence
<220> FEATURE:
<223> OTHER INFORMATION: protease cleavage site

<400> SEQUENCE: 55

Val Asn Pro Arg Gly Ile Val Thr
1               5

<210> SEQ ID NO 56
<211> LENGTH: 8
<212> TYPE: PRT
<213> ORGANISM: Artificial Sequence
<220> FEATURE:
<223> OTHER INFORMATION: protease cleavage site

<400> SEQUENCE: 56

Val Gln Pro Arg Ala Gln Lys Ile
1               5

<210> SEQ ID NO 57
<211> LENGTH: 8
<212> TYPE: PRT
<213> ORGANISM: Artificial Sequence
<220> FEATURE:
<223> OTHER INFORMATION: protease cleavage site

<400> SEQUENCE: 57

Val Ser Pro Arg Ala Ser Ala Ser
1               5

<210> SEQ ID NO 58
<211> LENGTH: 8
<212> TYPE: PRT
<213> ORGANISM: Artificial Sequence
<220> FEATURE:
<223> OTHER INFORMATION: protease cleavage site

<400> SEQUENCE: 58

Val Val Pro Arg Gly Val Asn Leu
1               5

<210> SEQ ID NO 59
<211> LENGTH: 8
<212> TYPE: PRT
<213> ORGANISM: Artificial Sequence
<220> FEATURE:
<223> OTHER INFORMATION: protease cleavage site

<400> SEQUENCE: 59

Trp Tyr Leu Arg Ser Asn Asn Gly
1               5

<210> SEQ ID NO 60
<211> LENGTH: 8
<212> TYPE: PRT
<213> ORGANISM: Artificial Sequence
<220> FEATURE:
<223> OTHER INFORMATION: protease cleavage site

<400> SEQUENCE: 60

Trp Tyr Leu Arg Ser Asn Thr Gly
1               5

```
<210> SEQ ID NO 61
<211> LENGTH: 8
<212> TYPE: PRT
<213> ORGANISM: Artificial Sequence
<220> FEATURE:
<223> OTHER INFORMATION: protease cleavage site

<400> SEQUENCE: 61

Ala Phe Trp Lys Thr Asp Ala Ser
 1               5

<210> SEQ ID NO 62
<211> LENGTH: 8
<212> TYPE: PRT
<213> ORGANISM: Artificial Sequence
<220> FEATURE:
<223> OTHER INFORMATION: protease cleavage site

<400> SEQUENCE: 62

Ile Glu Gly Arg Thr Ala Thr Ser
 1               5

<210> SEQ ID NO 63
<211> LENGTH: 8
<212> TYPE: PRT
<213> ORGANISM: Artificial Sequence
<220> FEATURE:
<223> OTHER INFORMATION: protease cleavage site

<400> SEQUENCE: 63

Thr Ala Ala Arg Gln Ser Thr Asn
 1               5

<210> SEQ ID NO 64
<211> LENGTH: 8
<212> TYPE: PRT
<213> ORGANISM: Artificial Sequence
<220> FEATURE:
<223> OTHER INFORMATION: protease cleavage site

<400> SEQUENCE: 64

Ile Asp Gly Arg Ile Val Glu Gly
 1               5

<210> SEQ ID NO 65
<211> LENGTH: 8
<212> TYPE: PRT
<213> ORGANISM: Artificial Sequence
<220> FEATURE:
<223> OTHER INFORMATION: protease cleavage site

<400> SEQUENCE: 65

Phe Asn Pro Arg Thr Phe Gly Ser
 1               5

<210> SEQ ID NO 66
<211> LENGTH: 8
<212> TYPE: PRT
<213> ORGANISM: Artificial Sequence
<220> FEATURE:
<223> OTHER INFORMATION: protease cleavage site

<400> SEQUENCE: 66

Arg Val Pro Lys Ser Phe Pro Phe
 1               5
```

```
<210> SEQ ID NO 67
<211> LENGTH: 8
<212> TYPE: PRT
<213> ORGANISM: Artificial Sequence
<220> FEATURE:
<223> OTHER INFORMATION: protease cleavage site

<400> SEQUENCE: 67

Pro Gln Leu Arg Met Lys Asn Asn
1               5

<210> SEQ ID NO 68
<211> LENGTH: 8
<212> TYPE: PRT
<213> ORGANISM: Artificial Sequence
<220> FEATURE:
<223> OTHER INFORMATION: protease cleavage site

<400> SEQUENCE: 68

Ser Ser Trp Arg Leu Thr Ser Ser
1               5

<210> SEQ ID NO 69
<211> LENGTH: 8
<212> TYPE: PRT
<213> ORGANISM: Artificial Sequence
<220> FEATURE:
<223> OTHER INFORMATION: protease cleavage site

<400> SEQUENCE: 69

Leu Gly Ile Arg Ser Phe Arg Asn
1               5

<210> SEQ ID NO 70
<211> LENGTH: 8
<212> TYPE: PRT
<213> ORGANISM: Artificial Sequence
<220> FEATURE:
<223> OTHER INFORMATION: protease cleavage site

<400> SEQUENCE: 70

Ala Met Ser Arg Met Ser Leu Ser
1               5

<210> SEQ ID NO 71
<211> LENGTH: 8
<212> TYPE: PRT
<213> ORGANISM: Artificial Sequence
<220> FEATURE:
<223> OTHER INFORMATION: protease cleavage site

<400> SEQUENCE: 71

Ala Asn Asn Arg Asp Asn Thr Tyr
1               5

<210> SEQ ID NO 72
<211> LENGTH: 8
<212> TYPE: PRT
<213> ORGANISM: Artificial Sequence
<220> FEATURE:
<223> OTHER INFORMATION: protease cleavage site

<400> SEQUENCE: 72

Ala Asn Val Arg Arg Lys Arg Tyr
1               5

<210> SEQ ID NO 73
```

```
<211> LENGTH: 8
<212> TYPE: PRT
<213> ORGANISM: Artificial Sequence
<220> FEATURE:
<223> OTHER INFORMATION: protease cleavage site

<400> SEQUENCE: 73

Ala Arg Gly Arg Ala Phe Pro Gln
 1               5

<210> SEQ ID NO 74
<211> LENGTH: 8
<212> TYPE: PRT
<213> ORGANISM: Artificial Sequence
<220> FEATURE:
<223> OTHER INFORMATION: protease cleavage site

<400> SEQUENCE: 74

Ala Thr Leu Lys Ser Arg Lys Met
 1               5

<210> SEQ ID NO 75
<211> LENGTH: 8
<212> TYPE: PRT
<213> ORGANISM: Artificial Sequence
<220> FEATURE:
<223> OTHER INFORMATION: protease cleavage site

<400> SEQUENCE: 75

Ala Thr Gln Lys Lys Val Glu Arg
 1               5

<210> SEQ ID NO 76
<211> LENGTH: 8
<212> TYPE: PRT
<213> ORGANISM: Artificial Sequence
<220> FEATURE:
<223> OTHER INFORMATION: protease cleavage site

<400> SEQUENCE: 76

Ala Thr Trp Lys Thr Arg Trp Tyr
 1               5

<210> SEQ ID NO 77
<211> LENGTH: 8
<212> TYPE: PRT
<213> ORGANISM: Artificial Sequence
<220> FEATURE:
<223> OTHER INFORMATION: protease cleavage site

<400> SEQUENCE: 77

Asp Val Gly Glu Tyr Asn Val Phe
 1               5

<210> SEQ ID NO 78
<211> LENGTH: 8
<212> TYPE: PRT
<213> ORGANISM: Artificial Sequence
<220> FEATURE:
<223> OTHER INFORMATION: protease cleavage site

<400> SEQUENCE: 78

Glu Ala Arg Gly Ser Val Ile Leu
 1               5

<210> SEQ ID NO 79
<211> LENGTH: 8
```

```
<212> TYPE: PRT
<213> ORGANISM: Artificial Sequence
<220> FEATURE:
<223> OTHER INFORMATION: protease cleavage site

<400> SEQUENCE: 79

Glu Ala Tyr Arg Arg Phe Tyr Gly
  1               5

<210> SEQ ID NO 80
<211> LENGTH: 8
<212> TYPE: PRT
<213> ORGANISM: Artificial Sequence
<220> FEATURE:
<223> OTHER INFORMATION: protease cleavage site

<400> SEQUENCE: 80

Glu Asp Asn Arg Asp Ser Ser Met
  1               5

<210> SEQ ID NO 81
<211> LENGTH: 8
<212> TYPE: PRT
<213> ORGANISM: Artificial Sequence
<220> FEATURE:
<223> OTHER INFORMATION: protease cleavage site

<400> SEQUENCE: 81

Glu Thr Leu Lys Val Ile Asp Glu
  1               5

<210> SEQ ID NO 82
<211> LENGTH: 8
<212> TYPE: PRT
<213> ORGANISM: Artificial Sequence
<220> FEATURE:
<223> OTHER INFORMATION: protease cleavage site

<400> SEQUENCE: 82

Phe Arg Ala Arg Ala Tyr Gly Phe
  1               5

<210> SEQ ID NO 83
<211> LENGTH: 8
<212> TYPE: PRT
<213> ORGANISM: Artificial Sequence
<220> FEATURE:
<223> OTHER INFORMATION: protease cleavage site

<400> SEQUENCE: 83

Gly Glu Ala Arg Gly Ser Val Ile
  1               5

<210> SEQ ID NO 84
<211> LENGTH: 8
<212> TYPE: PRT
<213> ORGANISM: Artificial Sequence
<220> FEATURE:
<223> OTHER INFORMATION: protease cleavage site

<400> SEQUENCE: 84

Gly Gly Tyr Arg Ala Arg Pro Ala
  1               5

<210> SEQ ID NO 85
<211> LENGTH: 8
<212> TYPE: PRT
```

```
<213> ORGANISM: Artificial Sequence
<220> FEATURE:
<223> OTHER INFORMATION: protease cleavage site

<400> SEQUENCE: 85

Gly Ile Leu Lys Glu Asn Ala Ala
 1               5

<210> SEQ ID NO 86
<211> LENGTH: 8
<212> TYPE: PRT
<213> ORGANISM: Artificial Sequence
<220> FEATURE:
<223> OTHER INFORMATION: protease cleavage site

<400> SEQUENCE: 86

Gly Pro Lys Arg Gly Thr Glu Pro
 1               5

<210> SEQ ID NO 87
<211> LENGTH: 8
<212> TYPE: PRT
<213> ORGANISM: Artificial Sequence
<220> FEATURE:
<223> OTHER INFORMATION: protease cleavage site

<400> SEQUENCE: 87

Ile Ile Arg Arg Ser Ile Gln Ile
 1               5

<210> SEQ ID NO 88
<211> LENGTH: 8
<212> TYPE: PRT
<213> ORGANISM: Artificial Sequence
<220> FEATURE:
<223> OTHER INFORMATION: protease cleavage site

<400> SEQUENCE: 88

Ile Thr Phe Arg Met Asn Val Ala
 1               5

<210> SEQ ID NO 89
<211> LENGTH: 8
<212> TYPE: PRT
<213> ORGANISM: Artificial Sequence
<220> FEATURE:
<223> OTHER INFORMATION: protease cleavage site

<400> SEQUENCE: 89

Lys His Ser Lys Arg His Ile His
 1               5

<210> SEQ ID NO 90
<211> LENGTH: 8
<212> TYPE: PRT
<213> ORGANISM: Artificial Sequence
<220> FEATURE:
<223> OTHER INFORMATION: protease cleavage site

<400> SEQUENCE: 90

Lys Lys Asp Arg Ala Arg Gln Glu
 1               5

<210> SEQ ID NO 91
<211> LENGTH: 8
<212> TYPE: PRT
<213> ORGANISM: Artificial Sequence
```

```
<220> FEATURE:
<223> OTHER INFORMATION: protease cleavage site

<400> SEQUENCE: 91

Lys Lys Pro Arg Cys Gly Val Pro
 1               5

<210> SEQ ID NO 92
<211> LENGTH: 8
<212> TYPE: PRT
<213> ORGANISM: Artificial Sequence
<220> FEATURE:
<223> OTHER INFORMATION: protease cleavage site

<400> SEQUENCE: 92

Lys Gln Val Lys Asp Asn Glu Asn
 1               5

<210> SEQ ID NO 93
<211> LENGTH: 8
<212> TYPE: PRT
<213> ORGANISM: Artificial Sequence
<220> FEATURE:
<223> OTHER INFORMATION: protease cleavage site

<400> SEQUENCE: 93

Leu Asp Pro Arg Ser Phe Leu Leu
 1               5

<210> SEQ ID NO 94
<211> LENGTH: 8
<212> TYPE: PRT
<213> ORGANISM: Artificial Sequence
<220> FEATURE:
<223> OTHER INFORMATION: protease cleavage site

<400> SEQUENCE: 94

Leu Pro Pro Lys Ser Gln Pro Pro
 1               5

<210> SEQ ID NO 95
<211> LENGTH: 8
<212> TYPE: PRT
<213> ORGANISM: Artificial Sequence
<220> FEATURE:
<223> OTHER INFORMATION: protease cleavage site

<400> SEQUENCE: 95

Leu Ser Phe Arg Ala Arg Ala Tyr
 1               5

<210> SEQ ID NO 96
<211> LENGTH: 8
<212> TYPE: PRT
<213> ORGANISM: Artificial Sequence
<220> FEATURE:
<223> OTHER INFORMATION: protease cleavage site

<400> SEQUENCE: 96

Met Ser Met Arg Val Arg Arg His
 1               5

<210> SEQ ID NO 97
<211> LENGTH: 8
<212> TYPE: PRT
<213> ORGANISM: Artificial Sequence
<220> FEATURE:
```

<223> OTHER INFORMATION: protease cleavage site

<400> SEQUENCE: 97

Asn Ser Gly Arg Ala Val Thr Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: protease cleavage site

<400> SEQUENCE: 98

Pro Ala Pro Arg Gly Tyr Pro Gly
1               5

<210> SEQ ID NO 99
<211> LENGTH: 8
<212> TYPE: PRT
<213> ORGANISM: Artificial Sequence
<220> FEATURE:
<223> OTHER INFORMATION: protease cleavage site

<400> SEQUENCE: 99

Pro Glu Ala Lys Ala Ser Cys Tyr
1               5

<210> SEQ ID NO 100
<211> LENGTH: 8
<212> TYPE: PRT
<213> ORGANISM: Artificial Sequence
<220> FEATURE:
<223> OTHER INFORMATION: protease cleavage site

<400> SEQUENCE: 100

Pro Glu Ser Lys Ala Thr Asn Ala
1               5

<210> SEQ ID NO 101
<211> LENGTH: 8
<212> TYPE: PRT
<213> ORGANISM: Artificial Sequence
<220> FEATURE:
<223> OTHER INFORMATION: protease cleavage site

<400> SEQUENCE: 101

Pro Gly Pro Lys Arg Gly Thr Glu
1               5

<210> SEQ ID NO 102
<211> LENGTH: 8
<212> TYPE: PRT
<213> ORGANISM: Artificial Sequence
<220> FEATURE:
<223> OTHER INFORMATION: protease cleavage site

<400> SEQUENCE: 102

Pro Lys Ala Lys Ser His Ala Pro
1               5

<210> SEQ ID NO 103
<211> LENGTH: 8
<212> TYPE: PRT
<213> ORGANISM: Artificial Sequence
<220> FEATURE:
<223> OTHER INFORMATION: protease cleavage site

<400> SEQUENCE: 103

Pro Leu Asp Lys Lys Arg Glu Glu
1               5

<210> SEQ ID NO 104
<211> LENGTH: 8
<212> TYPE: PRT
<213> ORGANISM: Artificial Sequence
<220> FEATURE:
<223> OTHER INFORMATION: protease cleavage site

<400> SEQUENCE: 104

Pro Leu Gln Lys Gln Leu Pro Ala
1               5

<210> SEQ ID NO 105
<211> LENGTH: 8
<212> TYPE: PRT
<213> ORGANISM: Artificial Sequence
<220> FEATURE:
<223> OTHER INFORMATION: protease cleavage site

<400> SEQUENCE: 105

Pro Gln Phe Arg Ile Lys Gly Gly
1               5

<210> SEQ ID NO 106
<211> LENGTH: 8
<212> TYPE: PRT
<213> ORGANISM: Artificial Sequence
<220> FEATURE:
<223> OTHER INFORMATION: protease cleavage site

<400> SEQUENCE: 106

Pro Gln Leu Arg Leu Pro His Thr
1               5

<210> SEQ ID NO 107
<211> LENGTH: 8
<212> TYPE: PRT
<213> ORGANISM: Artificial Sequence
<220> FEATURE:
<223> OTHER INFORMATION: protease cleavage site

<400> SEQUENCE: 107

Pro Gln Leu Arg Arg Gly Trp Arg
1               5

<210> SEQ ID NO 108
<211> LENGTH: 8
<212> TYPE: PRT
<213> ORGANISM: Artificial Sequence
<220> FEATURE:
<223> OTHER INFORMATION: protease cleavage site

<400> SEQUENCE: 108

Pro Gln Ser Arg Ser Val Pro Pro
1               5

<210> SEQ ID NO 109
<211> LENGTH: 8
<212> TYPE: PRT
<213> ORGANISM: Artificial Sequence
<220> FEATURE:
<223> OTHER INFORMATION: protease cleavage site

```
<400> SEQUENCE: 109

Pro Arg Phe Lys Ile Ile Gly Gly
1               5

<210> SEQ ID NO 110
<211> LENGTH: 8
<212> TYPE: PRT
<213> ORGANISM: Artificial Sequence
<220> FEATURE:
<223> OTHER INFORMATION: protease cleavage site

<400> SEQUENCE: 110

Pro Tyr Leu Lys Val Phe Asn Pro
1               5

<210> SEQ ID NO 111
<211> LENGTH: 8
<212> TYPE: PRT
<213> ORGANISM: Artificial Sequence
<220> FEATURE:
<223> OTHER INFORMATION: protease cleavage site

<400> SEQUENCE: 111

Gln Lys Ser Arg Asn Gly Leu Arg
1               5

<210> SEQ ID NO 112
<211> LENGTH: 8
<212> TYPE: PRT
<213> ORGANISM: Artificial Sequence
<220> FEATURE:
<223> OTHER INFORMATION: protease cleavage site

<400> SEQUENCE: 112

Gln Leu Ile Lys Ala Ile Gln Leu
1               5

<210> SEQ ID NO 113
<211> LENGTH: 8
<212> TYPE: PRT
<213> ORGANISM: Artificial Sequence
<220> FEATURE:
<223> OTHER INFORMATION: protease cleavage site

<400> SEQUENCE: 113

Gln Arg Tyr Lys Val Asp Tyr Glu
1               5

<210> SEQ ID NO 114
<211> LENGTH: 8
<212> TYPE: PRT
<213> ORGANISM: Artificial Sequence
<220> FEATURE:
<223> OTHER INFORMATION: protease cleavage site

<400> SEQUENCE: 114

Arg Ala Gln Arg Ser Ala Gly Ala
1               5

<210> SEQ ID NO 115
<211> LENGTH: 8
<212> TYPE: PRT
<213> ORGANISM: Artificial Sequence
<220> FEATURE:
<223> OTHER INFORMATION: protease cleavage site

<400> SEQUENCE: 115
```

Arg Gly Pro Arg Val Val Glu Arg
1               5

<210> SEQ ID NO 116
<211> LENGTH: 8
<212> TYPE: PRT
<213> ORGANISM: Artificial Sequence
<220> FEATURE:
<223> OTHER INFORMATION: protease cleavage site

<400> SEQUENCE: 116

Arg Pro Ala Lys Ala Ala Ala Thr
1               5

<210> SEQ ID NO 117
<211> LENGTH: 8
<212> TYPE: PRT
<213> ORGANISM: Artificial Sequence
<220> FEATURE:
<223> OTHER INFORMATION: protease cleavage site

<400> SEQUENCE: 117

Arg Arg Lys Arg Tyr Ala Ile Gln
1               5

<210> SEQ ID NO 118
<211> LENGTH: 8
<212> TYPE: PRT
<213> ORGANISM: Artificial Sequence
<220> FEATURE:
<223> OTHER INFORMATION: protease cleavage site

<400> SEQUENCE: 118

Arg Ser Ser Lys Gly Arg Ser Leu
1               5

<210> SEQ ID NO 119
<211> LENGTH: 8
<212> TYPE: PRT
<213> ORGANISM: Artificial Sequence
<220> FEATURE:
<223> OTHER INFORMATION: protease cleavage site

<400> SEQUENCE: 119

Arg Ser Thr Arg Phe Ala Ala Thr
1               5

<210> SEQ ID NO 120
<211> LENGTH: 8
<212> TYPE: PRT
<213> ORGANISM: Artificial Sequence
<220> FEATURE:
<223> OTHER INFORMATION: protease cleavage site

<400> SEQUENCE: 120

Ser Cys Asp Lys Thr His Thr Cys
1               5

<210> SEQ ID NO 121
<211> LENGTH: 8
<212> TYPE: PRT
<213> ORGANISM: Artificial Sequence
<220> FEATURE:
<223> OTHER INFORMATION: protease cleavage site

<400> SEQUENCE: 121

Ser Ile Asn Lys Ser Ser Pro Leu
1               5

<210> SEQ ID NO 122
<211> LENGTH: 8
<212> TYPE: PRT
<213> ORGANISM: Artificial Sequence
<220> FEATURE:
<223> OTHER INFORMATION: protease cleavage site

<400> SEQUENCE: 122

Ser Gln Pro Pro Glu Lys Thr Glu
1               5

<210> SEQ ID NO 123
<211> LENGTH: 8
<212> TYPE: PRT
<213> ORGANISM: Artificial Sequence
<220> FEATURE:
<223> OTHER INFORMATION: protease cleavage site

<400> SEQUENCE: 123

Ser Gln Arg Lys His Ser Lys Arg
1               5

<210> SEQ ID NO 124
<211> LENGTH: 8
<212> TYPE: PRT
<213> ORGANISM: Artificial Sequence
<220> FEATURE:
<223> OTHER INFORMATION: protease cleavage site

<400> SEQUENCE: 124

Ser Ser Met Lys Leu Ser Phe Arg
1               5

<210> SEQ ID NO 125
<211> LENGTH: 8
<212> TYPE: PRT
<213> ORGANISM: Artificial Sequence
<220> FEATURE:
<223> OTHER INFORMATION: protease cleavage site

<400> SEQUENCE: 125

Thr Glu Pro Lys Val Lys Leu Pro
1               5

<210> SEQ ID NO 126
<211> LENGTH: 8
<212> TYPE: PRT
<213> ORGANISM: Artificial Sequence
<220> FEATURE:
<223> OTHER INFORMATION: protease cleavage site

<400> SEQUENCE: 126

Thr Glu Tyr Arg Leu Val Ser Ile
1               5

<210> SEQ ID NO 127
<211> LENGTH: 8
<212> TYPE: PRT
<213> ORGANISM: Artificial Sequence
<220> FEATURE:
<223> OTHER INFORMATION: protease cleavage site

<400> SEQUENCE: 127

Thr His Glu Lys Gly Arg Gln Ser

```
1               5

<210> SEQ ID NO 128
<211> LENGTH: 8
<212> TYPE: PRT
<213> ORGANISM: Artificial Sequence
<220> FEATURE:
<223> OTHER INFORMATION: protease cleavage site

<400> SEQUENCE: 128

Thr Tyr Ser Lys Ala Ser Thr Pro
1               5

<210> SEQ ID NO 129
<211> LENGTH: 8
<212> TYPE: PRT
<213> ORGANISM: Artificial Sequence
<220> FEATURE:
<223> OTHER INFORMATION: protease cleavage site

<400> SEQUENCE: 129

Thr Tyr Ser Arg Ser Arg Tyr Leu
1               5

<210> SEQ ID NO 130
<211> LENGTH: 8
<212> TYPE: PRT
<213> ORGANISM: Artificial Sequence
<220> FEATURE:
<223> OTHER INFORMATION: protease cleavage site

<400> SEQUENCE: 130

Val Ser Asn Lys Val Ser Met Ser
1               5

<210> SEQ ID NO 131
<211> LENGTH: 228
<212> TYPE: PRT
<213> ORGANISM: Artificial Sequence
<220> FEATURE:
<223> OTHER INFORMATION: Fab-1 light chain

<400> SEQUENCE: 131

Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Trp Ser Thr Pro Val
                85                  90                  95

Phe Gly Gly Gly Thr Lys Leu Thr Val Leu Gly Gly Gly Ser Leu
            100                 105                 110

Val Pro Arg Gly Ser Gly Gly Gly Ser Gly Gln Pro Lys Ala Ala
            115                 120                 125

Pro Ser Val Thr Leu Phe Pro Pro Ser Ser Glu Glu Leu Gln Ala Asn
            130                 135                 140

Lys Ala Thr Leu Val Cys Leu Ile Ser Asp Phe Tyr Pro Gly Ala Val
```

```
                145                 150                 155                 160
Thr Val Ala Trp Lys Ala Asp Ser Ser Pro Val Lys Ala Gly Val Glu
                    165                 170                 175

Thr Thr Thr Pro Ser Lys Gln Ser Asn Asn Lys Tyr Ala Ala Ser Ser
                180                 185                 190

Tyr Leu Ser Leu Thr Pro Glu Gln Trp Lys Ser His Arg Ser Tyr Ser
                195                 200                 205

Cys Gln Val Thr His Glu Gly Ser Thr Val Glu Lys Thr Val Ala Pro
    210                 215                 220

Thr Glu Cys Ser
225

<210> SEQ ID NO 132
<211> LENGTH: 16
<212> TYPE: PRT
<213> ORGANISM: Artificial Sequence
<220> FEATURE:
<223> OTHER INFORMATION: protease cleavage site and linker

<400> SEQUENCE: 132

Gly Gly Gly Gly Ser Leu Val Pro Arg Gly Ser Gly Gly Gly Gly Ser
1               5                   10                  15

<210> SEQ ID NO 133
<211> LENGTH: 245
<212> TYPE: PRT
<213> ORGANISM: Artificial Sequence
<220> FEATURE:
<223> OTHER INFORMATION: Fab-1 heavy chain

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met Asp Trp Val Arg Gln Ala Pro Gly Lys Gly Leu Glu Trp Val
                35                  40                  45

Ser Ser Ile Arg Gly Ser Arg Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
                100                 105                 110

Val Thr Val Ser Ser Gly Gly Gly Gly Ser Leu Val Pro Arg Gly Ser
                115                 120                 125

Gly Gly Gly Gly Ser Ala Ser Thr Lys Gly Pro Ser Val Phe Pro Leu
                130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
                180                 185                 190

Ser Gly Leu Tyr Ser Leu Ser Ser Val Val Thr Val Pro Ser Ser Asn
                195                 200                 205
```

Phe Gly Thr Gln Thr Tyr Thr Cys Asn Val Asp His Lys Pro Ser Asn
    210                 215                 220

Thr Lys Val Asp Lys Thr Val Asp Tyr Lys Asp Asp Asp Lys His
225                 230                 235                 240

His His His His His
            245

<210> SEQ ID NO 134
<211> LENGTH: 1590
<212> TYPE: DNA
<213> ORGANISM: Artificial Sequence
<220> FEATURE:
<223> OTHER INFORMATION: sequence encoding Fab-1

<400> SEQUENCE: 134

```
ggtctcacat gaaaaaaacc gctatcgcta tcgccgtcgc actggctggc ttcgcaaccg      60
tggcacaggc atcctatgaa ctgacccaac gccgagtgt ctccgtgtca ccgggtcaga     120
cggcacgtat tacctgcagc ggtgataacc tgccgaaata ttacgcgcat ggtatcagc     180
aaaaaccggg ccaagccccg gtggttgtca tcttttatga cgttaatcgt ccgtccggta    240
tcccggaacg cttctcgggc agcaactctg gtaatacggc aaccctgacg atcagcggca    300
cccaggcaat ggatgaagct gactattact gtcaagcatg gtggagctct acgccggtgt    360
ttggcggtgg cacgaaactg accgtgctgg gtggcggtgg ctctctggtt ccgcgtggct    420
ccggtggcgg tggctcaggc agccgaaag cagcaccgag tgttaccctg tttccgccga    480
gttccgaaga actgcaagca aacaaagcta ccctggtgtg cctgattagc gatttctatc    540
cgggcgcagt tacggtcgcg tggaaagccg actcatcgcc ggtgaaagct ggtgttgaaa    600
ccacgacccc gtcaaaacag tcgaacaata aatatgcagc tagctcttac ctgtctctga    660
ccccggaaca gtggaaaagt catcgcagtt actcctgtca agttacgcac gaaggctcca    720
cggtcgaaaa aaccgtggca ccgacggaat gctcatgata agcatgcgta ggagaaaata    780
aaatgaaaca gtctaccatc gcactggcac tgctgccgct gctgtttacg ccggtgacca    840
aagcagaagt tcagctggtc gaaagtggtg gcggtctggt tcaaccgggc ggttcactgc    900
gtctgtcgtg cgcagcaagc ggttttacct tcagttccta tggtatggat tgggtccgtc    960
aggcaccggg taaaggtctg gaatgggtgt catcgattcg tggcagccgc ggttctacct   1020
attacgccga ttcagttaaa ggccgttta ccatctctcg cgacaacagt aaaaatacgc   1080
tgtatctgca gatgaacagc ctgcgcgcgg aagataccgc cgtgtattac tgtgcccgtc   1140
tgtatcgcta ctggttcgac tactggggcc agggtacgct ggtgaccgtt agctctggcg   1200
gtggcggttc gctggtcccg cgtggcagcg gcggtggcgg ttcagcgagc accaaaggtc   1260
cgagcgtgtt tccgctggca ccgtcagcc gctctaccag tgaatccacg gcagctctgg   1320
gttgtctggt gaaagattat tttccggaac cggtcaccgt gagttggaac tccggcgcac   1380
tgacctcggg tgttcatacg ttcccggctg tcctgcagag ttccggcctg tatagcctgt   1440
catcggtggt taccgttccg agctctaatt tcggcaccca aacgtacacc tgcaacgtcg   1500
atcacaaacc gtctaatacc aaagttgaca aacggttga ttacaaagac gacgacgaca    1560
aacaccacca ccaccaccat tgataagctt                                    1590
```

<210> SEQ ID NO 135
<211> LENGTH: 218
<212> TYPE: PRT
<213> ORGANISM: Artificial Sequence
<220> FEATURE:

<223> OTHER INFORMATION: Fab-2 light chain

<400> SEQUENCE: 135

```
Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Trp Ser Ser Thr Pro Val
                85                  90                  95

Phe Gly Gly Gly Thr Lys Leu Thr Val Leu Val Pro Arg Gly Ser
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 136
<211> LENGTH: 235
<212> TYPE: PRT
<213> ORGANISM: Artificial Sequence
<220> FEATURE:
<223> OTHER INFORMATION: Fab-2 Heavy Chain

<400> SEQUENCE: 136

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Arg Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser Leu Val Pro Arg Gly Ser Ala Ser Thr Lys Gly
        115                 120                 125
```

```
Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Asp Tyr Lys
    210                 215                 220

Asp Asp Asp Asp Lys His His His His His His
225                 230                 235
```

<210> SEQ ID NO 137
<211> LENGTH: 6
<212> TYPE: PRT
<213> ORGANISM: Artificial Sequence
<220> FEATURE:
<223> OTHER INFORMATION: protease cleavage site

<400> SEQUENCE: 137

```
Leu Val Pro Arg Gly Ser
 1               5
```

<210> SEQ ID NO 138
<211> LENGTH: 1530
<212> TYPE: DNA
<213> ORGANISM: Artificial Sequence
<220> FEATURE:
<223> OTHER INFORMATION: Fab-2 coding sequence

<400> SEQUENCE: 138

```
ggtctcacat gaaaaaaacg gctatcgcaa tcgctgtggc actggcaggc ttcgcaacgg      60
tcgcgcaggc atcctatgaa ctgacgcaac cgccgagtgt ctccgtgtca ccgggtcaga     120
cggcacgtat tacctgctct ggtgataacc tgccgaaata ttacgcgcat ggtatcagc     180 aaaaaccggg ccaagccccg gtggttgtca tcttttatga cgttaatcgt ccgtcgggta     240
tcccggaacg cttctcgggc agcaactctg gtaatacggc caccctgacg atctcaggca     300
cccaggcaat ggatgaagct gactattact gccaagcatg gtggagctct acgccggtgt     360
ttggcggtgg cacgaaactg accgttctgc ggtcccgcg tggctccggt cagccgaaag     420
cagccccgtc agttaccctg tttccgccga gttccgaaga actgcaagca acaaagcta     480 ccctggtgtg tctgattagc gatttctatc cgggcgcagt tacggtcgcg tggaaagccg     540
actcatcgcc ggtcaaagct ggtgtggaaa ccaccacccc gtcaaaacag tcgaacaata     600
aatatgcagc tagctcttac ctgtcgctga ccccggaaca gtggaaaagc catcgcagtt     660
actcctgcca agttacgcac gaaggctcta cggttgaaaa aaccgtcgca ccgacggaat     720
gcagttgata agcatgcgta ggagaaaata aatgaaaca gagcaccatc gcactggcac     780
tgctgccgct gctgtttacg ccggtcacca agcagaagt gcagctggtt gaatctggtg     840
gcggtctggt gcaaccgggc ggttcactgc gtctgtcgtg tgcggccagc ggctttacct     900
tcagttccta tggtatggat tgggtccgtc aggcaccggg taaggtctg aatgggtgt     960 catcgattcg tggcagccgc ggttctacct attacgccga ttccgttaaa ggccgtttca    1020
```

```
ccatctctcg cgacaacagt aaaaatacgc tgtatctgca gatgaacagt ctgcgcgcgg   1080
aagataccgc cgtgtattac tgcgcccgtc tgtatcgcta ctggtttgac tactggggcc   1140
agggtacgct ggtgaccgtt agctctctgg ttccgcgtgg ctcagcgagc accaaaggtc   1200
cgagtgtctt cccgctggca ccgtgcagcc gctctaccag tgaatccacg cagctctgg    1260 gttgtctggt gaaagattat tttccggaac cggtcaccgt gagttggaac tccggcgcac   1320
tgacctccgg tgtgcatacg ttcccggctg ttctgcagag ttccggcctg tattcactgt   1380
catcggtggt taccgtgccg agctctaatt ttggcaccca aacgtacacc tgtaacgttg   1440
atcacaaacc gagcaatacc aaagttgaca aaccgttga ctacaaagac gacgacgaca    1500
aacaccacca ccaccaccac tgataagctt                                    1530
```

<210> SEQ ID NO 139
<211> LENGTH: 228
<212> TYPE: PRT
<213> ORGANISM: Artificial Sequence
<220> FEATURE:
<223> OTHER INFORMATION: IgG2-linker 1, Light chain amino acid sequence

<400> SEQUENCE: 139

```
Ser Tyr Glu Leu Thr Gln Pro Pro Ser Val Ser Val Ser Pro Gly Gln
  1               5                  10                  15

Thr Ala Arg Ile Thr Cys Ser Gly Asp Asn Leu Pro Lys Tyr Tyr Ala
             20                  25                  30

His Trp Tyr Gln Gln Lys Pro Gly Gln Ala Pro Val Val Val Ile Phe
         35                  40                  45

Tyr Asp Val Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Trp Ser Thr Pro Val
                 85                  90                  95

Phe Gly Gly Gly Thr Lys Leu Thr Val Leu Gly Gly Gly Ser Leu
            100                 105                 110

Val Pro Arg Gly Ser Gly Gly Gly Ser Gly Gln Pro Lys Ala Ala
        115                 120                 125

Pro Ser Val Thr Leu Phe Pro Pro Ser Ser Glu Glu Leu Gln Ala Asn
    130                 135                 140

Lys Ala Thr Leu Val Cys Leu Ile Ser Asp Phe Tyr Pro Gly Ala Val
145                 150                 155                 160

Thr Val Ala Trp Lys Ala Asp Ser Ser Pro Val Lys Ala Gly Val Glu
                165                 170                 175

Thr Thr Thr Pro Ser Lys Gln Ser Asn Asn Lys Tyr Ala Ala Ser Ser
            180                 185                 190

Tyr Leu Ser Leu Thr Pro Glu Gln Trp Lys Ser His Arg Ser Tyr Ser
        195                 200                 205

Cys Gln Val Thr His Glu Gly Ser Thr Val Glu Lys Thr Val Ala Pro
    210                 215                 220

Thr Glu Cys Ser
225
```

<210> SEQ ID NO 140
<211> LENGTH: 458
<212> TYPE: PRT
<213> ORGANISM: Artificial Sequence
<220> FEATURE:

<223> OTHER INFORMATION: IgG2-linker1, heavy chain amino acid sequence

<400> SEQUENCE: 140

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Gly | Met | Asp | Trp | Val | Arg | Gln | Ala | Pro | Gly | Lys | Gly | Leu | Glu | Trp | Val |
| | | | 35 | | | | | 40 | | | | | 45 | | |
| Ser | Ser | Ile | Arg | Gly | Ser | Arg | Gly | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Leu | Tyr | Arg | Tyr | Trp | Phe | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Gly | Gly | Gly | Gly | Ser | Leu | Val | Pro | Arg |
| | | | 115 | | | | | 120 | | | | | 125 | | |
| Gly | Ser | Gly | Gly | Gly | Gly | Ser | Thr | Lys | Gly | Pro | Ser | Val | Phe | Pro | Leu |
| | 130 | | | | | 135 | | | | | 140 | | | | |
| Ala | Pro | Cys | Ser | Arg | Ser | Thr | Ser | Glu | Ser | Thr | Ala | Ala | Leu | Gly | Cys |
| 145 | | | | | 150 | | | | | 155 | | | | | 160 |
| Leu | Val | Lys | Asp | Tyr | Phe | Pro | Glu | Pro | Val | Thr | Val | Ser | Trp | Asn | Ser |
| | | | | 165 | | | | | 170 | | | | | 175 | |
| Gly | Ala | Leu | Thr | Ser | Gly | Val | His | Thr | Phe | Pro | Ala | Val | Leu | Gln | Ser |
| | | | 180 | | | | | 185 | | | | | 190 | | |
| Ser | Gly | Leu | Tyr | Ser | Leu | Ser | Ser | Val | Val | Thr | Val | Pro | Ser | Ser | Asn |
| | | | 195 | | | | | 200 | | | | | 205 | | |
| Phe | Gly | Thr | Gln | Thr | Tyr | Thr | Cys | Asn | Val | Asp | His | Lys | Pro | Ser | Asn |
| | 210 | | | | | 215 | | | | | 220 | | | | |
| Thr | Lys | Val | Asp | Lys | Thr | Val | Glu | Arg | Lys | Cys | Cys | Val | Glu | Cys | Pro |
| 225 | | | | | 230 | | | | | 235 | | | | | 240 |
| Pro | Cys | Pro | Ala | Pro | Pro | Val | Ala | Gly | Pro | Ser | Val | Phe | Leu | Phe | Pro |
| | | | | 245 | | | | | 250 | | | | | 255 | |
| Pro | Lys | Pro | Lys | Asp | Thr | Leu | Met | Ile | Ser | Arg | Thr | Pro | Glu | Val | Thr |
| | | | 260 | | | | | 265 | | | | | 270 | | |
| Cys | Val | Val | Val | Asp | Val | Ser | His | Glu | Asp | Pro | Glu | Val | Gln | Phe | Asn |
| | | | 275 | | | | | 280 | | | | | 285 | | |
| Trp | Tyr | Val | Asp | Gly | Val | Glu | Val | His | Asn | Ala | Lys | Thr | Lys | Pro | Arg |
| | 290 | | | | | 295 | | | | | 300 | | | | |
| Glu | Glu | Gln | Phe | Asn | Ser | Thr | Phe | Arg | Val | Val | Ser | Val | Leu | Thr | Val |
| 305 | | | | | 310 | | | | | 315 | | | | | 320 |
| Val | His | Gln | Asp | Trp | Leu | Asn | Gly | Lys | Glu | Tyr | Lys | Cys | Lys | Val | Ser |
| | | | | 325 | | | | | 330 | | | | | 335 | |
| Asn | Lys | Gly | Leu | Pro | Ala | Pro | Ile | Glu | Lys | Thr | Ile | Ser | Lys | Thr | Lys |
| | | | 340 | | | | | 345 | | | | | 350 | | |
| Gly | Gln | Pro | Arg | Glu | Pro | Gln | Val | Tyr | Thr | Leu | Pro | Pro | Ser | Arg | Glu |
| | | | 355 | | | | | 360 | | | | | 365 | | |
| Glu | Met | Thr | Lys | Asn | Gln | Val | Ser | Leu | Thr | Cys | Leu | Val | Lys | Gly | Phe |
| | 370 | | | | | 375 | | | | | 380 | | | | |
| Tyr | Pro | Ser | Asp | Ile | Ala | Val | Glu | Trp | Glu | Ser | Asn | Gly | Gln | Pro | Glu |
| 385 | | | | | 390 | | | | | 395 | | | | | 400 |

```
Asn Asn Tyr Lys Thr Thr Pro Pro Met Leu Asp Ser Asp Gly Ser Phe
            405                 410                 415

Phe Leu Tyr Ser Lys Leu Thr Val Asp Lys Ser Arg Trp Gln Gln Gly
        420                 425                 430

Asn Val Phe Ser Cys Ser Val Met His Glu Ala Leu His Asn His Tyr
        435                 440                 445

Thr Gln Lys Ser Leu Ser Leu Ser Pro Gly
        450                 455
```

<210> SEQ ID NO 141
<211> LENGTH: 684
<212> TYPE: DNA
<213> ORGANISM: Artificial Sequence
<220> FEATURE:
<223> OTHER INFORMATION: IgG2-linker 1, Light chain DNA sequence

<400> SEQUENCE: 141

| | | |
|---|---|---|
| tcctacgagc tgacccagcc cccttccgtg tccgtgtctc ctggccagac cgcccggatc | 60 |
| acctgttccg gcgacaacct gcccaagtac tacgcccact ggtatcagca gaagcccggc | 120 |
| caggccccg tggtggtcat cttctacgac gtgaaccggc cctccggcat ccccgagaga | 180 |
| ttctccggct ccaactccgg caacaccgcc accctgacca tctccggcac ccaggccatg | 240 |
| gacgaggccg actactactg ccaggcttgg tggtcctcca ccccgtgtt tggcggcgga | 300 |
| acaaagttaa ccgtgctggg cggtggagga tcactggttc cgcgtggctc tggcggtgga | 360 |
| ggatcaggcc agcccaaggc cgctccttcc gtgaccctgt tccccccatc ctccgaggaa | 420 |
| ctgcaggcca caaggccac cctggtctgc ctgatctccg acttctaccc tggcgccgtg | 480 |
| accgtggcct ggaaggccga cagctctcct gtgaaggccg gcgtggaaac caccaccccc | 540 |
| tccaagcagt ccaacaacaa atacgccgcc tcctcctacc tgtccctgac ccccgagcag | 600 |
| tggaagtccc accggtccta cagctgccag gtcacacacg agggctccac cgtggaaaag | 660 |
| acagtggccc ccaccgagtg ctct | 684 |

<210> SEQ ID NO 142
<211> LENGTH: 1374
<212> TYPE: DNA
<213> ORGANISM: Artificial Sequence
<220> FEATURE:
<223> OTHER INFORMATION: IgG2-linker 1, Heavy chain DNA sequence

<400> SEQUENCE: 142

| | | |
|---|---|---|
| gaggtgcagc tggtggaatc cggcggaggc ctggtccagc ctggcggatc tctgagactg | 60 |
| tcctgcgccg cctccggctt caccttctcc agctacggca tggactgggt ccgacaggcc | 120 |
| cctggcaagg gcctggaatg ggtgtcctcc atcggggct ctcggggctc cacctactac | 180 |
| gccgactccg tgaagggccg gttcaccatc tcccgggaca actccaagaa caccctgtac | 240 |
| ctgcagatga actccctgcg ggccgaggac accgccgtgt actactgcgc cagactgtac | 300 |
| cggtattggt tcgactactg gggccagggc accctggtca ccgtcagctc agcttctggc | 360 |
| ggaggcggct ctctggtgcc tagaggatct ggcggcggag ctccaccaa gggcccttcc | 420 |
| gtgttccctc tggccccttg ctcccggtcc acctccgagt ctaccgccgc tctgggctgc | 480 |
| ctggtcaagg attacttccc cgagccgtg accgtgtcct ggaactctgg cgccctgacc | 540 |
| agcggcgtgc acaccttccc tgccgtgctg cagtcctccg gcctgtactc cctgtcctcc | 600 |
| gtcgtgacag tgccctcctc caacttcggc acccagacct acacctgtaa cgtggaccac | 660 |
| aagccctcca caccaaggt ggacaagacc gtggaacgga gtgctgcgt ggaatgcccc | 720 |

```
cctgtcctg cacctcctgt ggctggacct agcgtgttcc tgttcccccc aaagcccaag    780
gacaccctga tgatctcccg gaccccgaa gtgacctgcg tggtggtgga cgtgtcccac    840 gaggacccg aggtgcagtt caattggtac gtggacggcg tggaagtgca acgccaag     900 accaagccca gagaggaaca gttcaactcc accttccggg tggtgtccgt gctgaccgtg    960
gtgcaccagg actggctgaa cggcaaagag tacaagtgca aggtctccaa caagggcctg   1020
cctgccccca tcgaaaagac catcagcaag accaagggcc agccccgcga gccccaggtg   1080
tacacactgc cacctagccg ggaagagatg accaagaacc aggtgtccct gacctgtctg   1140
gtcaagggct tctacccatc cgacattgcc gtgaatggg agtccaacgg ccagcccgag    1200
aacaactaca agaccaccc ccccatgctg gactccgacg gctcattctt cctgtactcc   1260
aagctgacag tggacaagtc ccggtggcag cagggcaacg tgttctcctg ctccgtgatg   1320
cacgaggccc tgcacaacca ctacacccag aagtccctgt ccctgagccc cggc        1374
```

<210> SEQ ID NO 143
<211> LENGTH: 218
<212> TYPE: PRT
<213> ORGANISM: Artificial Sequence
<220> FEATURE:
<223> OTHER INFORMATION: IgG2-linker 2, Light chain amino acid sequence

<400> SEQUENCE: 143

```
Ser Tyr Glu Leu Thr Gln Pro Pro Ser Val Ser Val Ser Pro Gly Gln
  1               5                  10                  15

Thr Ala Arg Ile Thr Cys Ser Gly Asp Asn Leu Pro Lys Tyr Tyr Ala
             20                  25                  30

His Trp Tyr Gln Gln Lys Pro Gly Gln Ala Pro Val Val Val Ile Phe
         35                  40                  45

Tyr Asp Val Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Trp Ser Ser Thr Pro Val
                 85                  90                  95

Phe Gly Gly Gly Thr Lys Leu Thr Val Leu Leu Val Pro Arg Gly Ser
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 144
<211> LENGTH: 448
<212> TYPE: PRT

<213> ORGANISM: Artificial Sequence
<220> FEATURE:
<223> OTHER INFORMATION: IgG2-linker 2, heavy chain amino acid sequence

<400> SEQUENCE: 144

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gly Met Asp Trp Val Arg Gln Ala Pro Gly Lys Gly Leu Glu Trp Val
         35                  40                  45

Ser Ser Ile Arg Gly Ser Arg Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Leu Tyr Arg Tyr Trp Phe Asp Tyr Trp Gly Gln Gly Thr Leu
            100                 105                 110

Val Thr Val Ser Ser Ala Ser Leu Val Pro Arg Gly Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
```

```
              385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 145
<211> LENGTH: 654
<212> TYPE: DNA
<213> ORGANISM: Artificial Sequence
<220> FEATURE:
<223> OTHER INFORMATION: IgG2-linker 2, Light chain DNA sequence

<400> SEQUENCE: 145

| | |
|---|---|
| tcctacgagc tgacccagcc cccttccgtg tccgtgtctc ctggccagac cgcccggatc | 60 |
| acctgttccg gcgacaacct gcccaagtac tacgcccact ggtatcagca gaagcccggc | 120 |
| caggcccccg tggtggtcat cttctacgac gtgaaccggc cctccggcat ccccgagaga | 180 |
| ttctccggct ccaactccgg caacaccgcc accctgacca tctccggcac ccaggccatg | 240 |
| gacgaggccg actactactg ccaggcttgg tggtcctcca ccccgtgtt tggcggcgga | 300 |
| acaaagttaa ccgtgctgct ggttccgcgt ggctctggcc agcccaaggc cgctccttcc | 360 |
| gtgaccctgt tccccccatc ctccgaggaa ctgcaggcca acaaggccac cctggtctgc | 420 |
| ctgatctccg acttctaccc tggcgccgtg accgtggcct ggaaggccga cagctctcct | 480 |
| gtgaaggccg gcgtggaaac caccacccc tccaagcagt ccaacaacaa atacgccgcc | 540 |
| tcctcctacc tgtccctgac ccccgagcag tggaagtccc accggtccta cagctgccag | 600 |
| gtcacacacg agggctccac cgtggaaaag acagtggccc caccgagtg ctct | 654 |

<210> SEQ ID NO 146
<211> LENGTH: 1344
<212> TYPE: DNA
<213> ORGANISM: Artificial Sequence
<220> FEATURE:
<223> OTHER INFORMATION: IgG2-linker 2, Heavy chain DNA sequence

<400> SEQUENCE: 146

| | |
|---|---|
| gaggtgcagc tggtggaatc cggcggaggc ctggtccagc ctggcggatc tctgagactg | 60 |
| tcctgcgccg cctccggctt caccttctcc agctacggca tggactgggt ccgacaggcc | 120 |
| cctggcaagg gcctggaatg gtgtcctcc atccggggct ctcggggctc cacctactac | 180 |
| gccgactccg tgaagggccg gttcaccatc tcccgggaca actccaagaa caccctgtac | 240 |
| ctgcagatga actccctgcg ggccgaggac accgccgtgt actactgcgc cagactgtac | 300 |
| cggtattggt tcgactactg gggccagggc accctggtca ccgtcagctc agcttctctg | 360 |
| gtgcctagag gatctaccaa ggccccttcc gtgttccctc tggcccttg ctccggtcc | 420 |
| acctccgagt ctaccgccgc tctgggctgc ctggtcaagg attacttccc cgagcccgtg | 480 |
| accgtgtcct ggaactctgg cgccctgacc agcggcgtgc acccttcc tgccgtgctg | 540 |
| cagtcctccg gcctgtactc cctgtcctcc gtcgtgacag tgcccctctc aacttcggc | 600 |
| acccagacct acacctgtaa cgtggaccac aagccctcca caccaaggt ggacaagacc | 660 |
| gtggaacgga agtgctgcgt ggaatgcccc cctgtcctg cacctcctgt ggctggacct | 720 |
| agcgtgttcc tgttcccccc aaagcccaag gacaccctga tgatctcccg gacccccgaa | 780 |

-continued

| | |
|---|---|
| gtgacctgcg tggtggtgga cgtgtcccac gaggacccc g aggtgcagtt caattggtac | 840 |
| gtggacggcg tggaagtgca caacgccaag accaagccca gagaggaaca gttcaactcc | 900 |
| accttccggg tggtgtccgt gctgaccgtg gtgcaccagg actggctgaa cggcaaagag | 960 |
| tacaagtgca aggtctccaa caagggcctg cctgccccca tcgaaaagac catcagcaag | 1020 |
| accaagggcc agccccgcga gccccaggtg tacacactgc cacctagccg ggaagagatg | 1080 |
| accaagaacc aggtgtccct gacctgtctg gtcaagggct tctacccatc cgacattgcc | 1140 |
| gtggaatggg agtccaacgg ccagcccgag aacaactaca gaccaccccc ccccatgctg | 1200 |
| gactccgacg gctcattctt cctgtactcc aagctgacag tggacaagtc ccggtggcag | 1260 |
| cagggcaacg tgttctcctg ctccgtgatg cacgaggccc tgcacaacca ctacacccag | 1320 |
| aagtccctgt ccctgagccc cggc | 1344 |

<210> SEQ ID NO 147
<211> LENGTH: 6
<212> TYPE: PRT
<213> ORGANISM: Artificial Sequence
<220> FEATURE:
<223> OTHER INFORMATION: Thrombin cleavage site
<221> NAME/KEY: VARIANT
<222> LOCATION: (1)...(2)
<223> OTHER INFORMATION: Xaa = hydrophobic amino acid
<221> NAME/KEY: VARIANT
<222> LOCATION: (5)...(6)
<223> OTHER INFORMATION: Xaa = nonacidic amino acid

<400> SEQUENCE: 147

Xaa Xaa Pro Arg Xaa Xaa
 1               5

<210> SEQ ID NO 148
<211> LENGTH: 4
<212> TYPE: PRT
<213> ORGANISM: Artificial Sequence
<220> FEATURE:
<223> OTHER INFORMATION: Factor Xa cleavage site
<221> NAME/KEY: VARIANT
<222> LOCATION: (2)...(2)
<223> OTHER INFORMATION: Xaa = Glu or Asp

<400> SEQUENCE: 148

Ile Xaa Gly Arg
 1

<210> SEQ ID NO 149
<211> LENGTH: 5
<212> TYPE: PRT
<213> ORGANISM: Artificial Sequence
<220> FEATURE:
<223> OTHER INFORMATION: amino acid linker

<400> SEQUENCE: 149

Gly Gly Gly Gly Ser
 1               5

<210> SEQ ID NO 150
<211> LENGTH: 58
<212> TYPE: PRT
<213> ORGANISM: Artificial Sequence
<220> FEATURE:
<223> OTHER INFORMATION: amino acids 95-152 of SEQ ID NO:133

<400> SEQUENCE: 150

Tyr Cys Ala Arg Leu Tyr Arg Tyr Trp Phe Asp Tyr Trp Gly Gln Gly

```
                1               5                  10                  15
            Thr Leu Val Thr Val Ser Ser Ala Ser Gly Ser Gly Gly Gly Leu Val
                        20                  25                  30
            Pro Arg Gly Ser Gly Gly Gly Ser Thr Lys Gly Pro Ser Val Phe
                    35                  40                  45
            Pro Leu Ala Pro Cys Ser Arg Ser Thr Ser
                    50                  55

<210> SEQ ID NO 151
<211> LENGTH: 16
<212> TYPE: PRT
<213> ORGANISM: Artificial Sequence
<220> FEATURE:
<223> OTHER INFORMATION: amino acid linker

<400> SEQUENCE: 151

Ala Lys Thr Thr Pro Lys Leu Glu Glu Gly Glu Phe Ser Glu Ala Arg
1               5                   10                  15

<210> SEQ ID NO 152
<211> LENGTH: 17
<212> TYPE: PRT
<213> ORGANISM: Artificial Sequence
<220> FEATURE:
<223> OTHER INFORMATION: amino acid linker

<400> SEQUENCE: 152

Ala Lys Thr Thr Pro Lys Leu Glu Glu Gly Glu Phe Ser Glu Ala Arg
1               5                   10                  15
Val

<210> SEQ ID NO 153
<211> LENGTH: 9
<212> TYPE: PRT
<213> ORGANISM: Artificial Sequence
<220> FEATURE:
<223> OTHER INFORMATION: amino acid linker

<400> SEQUENCE: 153

Ala Lys Thr Thr Pro Lys Leu Gly Gly
1               5

<210> SEQ ID NO 154
<211> LENGTH: 10
<212> TYPE: PRT
<213> ORGANISM: Artificial Sequence
<220> FEATURE:
<223> OTHER INFORMATION: amino acid linker

<400> SEQUENCE: 154

Ser Ala Lys Thr Thr Pro Lys Leu Gly Gly
1               5                   10

<210> SEQ ID NO 155
<211> LENGTH: 6
<212> TYPE: PRT
<213> ORGANISM: Artificial Sequence
<220> FEATURE:
<223> OTHER INFORMATION: amino acid linker

<400> SEQUENCE: 155

Ser Ala Lys Thr Thr Pro
1               5
```

```
<210> SEQ ID NO 156
<211> LENGTH: 6
<212> TYPE: PRT
<213> ORGANISM: Artificial Sequence
<220> FEATURE:
<223> OTHER INFORMATION: amino acid linker

<400> SEQUENCE: 156

Arg Ala Asp Ala Ala Pro
 1               5

<210> SEQ ID NO 157
<211> LENGTH: 9
<212> TYPE: PRT
<213> ORGANISM: Artificial Sequence
<220> FEATURE:
<223> OTHER INFORMATION: amino acid linker

<400> SEQUENCE: 157

Arg Ala Asp Ala Ala Pro Thr Val Ser
 1               5

<210> SEQ ID NO 158
<211> LENGTH: 12
<212> TYPE: PRT
<213> ORGANISM: Artificial Sequence
<220> FEATURE:
<223> OTHER INFORMATION: amino acid linker

<400> SEQUENCE: 158

Arg Ala Asp Ala Ala Ala Ala Gly Gly Pro Gly Ser
 1               5                  10

<210> SEQ ID NO 159
<211> LENGTH: 27
<212> TYPE: PRT
<213> ORGANISM: Artificial Sequence
<220> FEATURE:
<223> OTHER INFORMATION: amino acid linker

<400> SEQUENCE: 159

Arg Ala Asp Ala Ala Ala Ala Gly Gly Gly Gly Ser Gly Gly Gly Gly
 1               5                  10                  15

Ser Gly Gly Gly Gly Ser Gly Gly Gly Gly Ser
                20                  25

<210> SEQ ID NO 160
<211> LENGTH: 18
<212> TYPE: PRT
<213> ORGANISM: Artificial Sequence
<220> FEATURE:
<223> OTHER INFORMATION: amino acid linker

<400> SEQUENCE: 160

Ser Ala Lys Thr Thr Pro Lys Leu Glu Glu Gly Glu Phe Ser Glu Ala
 1               5                  10                  15

Arg Val

<210> SEQ ID NO 161
<211> LENGTH: 5
<212> TYPE: PRT
<213> ORGANISM: Artificial Sequence
<220> FEATURE:
<223> OTHER INFORMATION: amino acid linker

<400> SEQUENCE: 161
```

```
Ala Asp Ala Ala Pro
1               5

<210> SEQ ID NO 162
<211> LENGTH: 12
<212> TYPE: PRT
<213> ORGANISM: Artificial Sequence
<220> FEATURE:
<223> OTHER INFORMATION: amino acid linker

<400> SEQUENCE: 162

Ala Asp Ala Ala Pro Thr Val Ser Ile Phe Pro Pro
1               5                   10

<210> SEQ ID NO 163
<211> LENGTH: 5
<212> TYPE: PRT
<213> ORGANISM: Artificial Sequence
<220> FEATURE:
<223> OTHER INFORMATION: amino acid linker

<400> SEQUENCE: 163

Thr Val Ala Ala Pro
1               5

<210> SEQ ID NO 164
<211> LENGTH: 12
<212> TYPE: PRT
<213> ORGANISM: Artificial Sequence
<220> FEATURE:
<223> OTHER INFORMATION: amino acid linker

<400> SEQUENCE: 164

Thr Val Ala Ala Pro Ser Val Phe Ile Phe Pro Pro
1               5                   10

<210> SEQ ID NO 165
<211> LENGTH: 6
<212> TYPE: PRT
<213> ORGANISM: Artificial Sequence
<220> FEATURE:
<223> OTHER INFORMATION: amino acid linker

<400> SEQUENCE: 165

Gln Pro Lys Ala Ala Pro
1               5

<210> SEQ ID NO 166
<211> LENGTH: 13
<212> TYPE: PRT
<213> ORGANISM: Artificial Sequence
<220> FEATURE:
<223> OTHER INFORMATION: amino acid linker

<400> SEQUENCE: 166

Gln Pro Lys Ala Ala Pro Ser Val Thr Leu Phe Pro Pro
1               5                   10

<210> SEQ ID NO 167
<211> LENGTH: 6
<212> TYPE: PRT
<213> ORGANISM: Artificial Sequence
<220> FEATURE:
<223> OTHER INFORMATION: amino acid linker

<400> SEQUENCE: 167

Ala Lys Thr Thr Pro Pro
```

```
1               5

<210> SEQ ID NO 168
<211> LENGTH: 13
<212> TYPE: PRT
<213> ORGANISM: Artificial Sequence
<220> FEATURE:
<223> OTHER INFORMATION: amino acid linker

<400> SEQUENCE: 168

Ala Lys Thr Thr Pro Pro Ser Val Thr Pro Leu Ala Pro
1               5                   10

<210> SEQ ID NO 169
<211> LENGTH: 6
<212> TYPE: PRT
<213> ORGANISM: Artificial Sequence
<220> FEATURE:
<223> OTHER INFORMATION: amino acid linker

<400> SEQUENCE: 169

Ala Lys Thr Thr Ala Pro
1               5

<210> SEQ ID NO 170
<211> LENGTH: 13
<212> TYPE: PRT
<213> ORGANISM: Artificial Sequence
<220> FEATURE:
<223> OTHER INFORMATION: amino acid linker

<400> SEQUENCE: 170

Ala Lys Thr Thr Ala Pro Ser Val Tyr Pro Leu Ala Pro
1               5                   10

<210> SEQ ID NO 171
<211> LENGTH: 6
<212> TYPE: PRT
<213> ORGANISM: Artificial Sequence
<220> FEATURE:
<223> OTHER INFORMATION: amino acid linker

<400> SEQUENCE: 171

Ala Ser Thr Lys Gly Pro
1               5

<210> SEQ ID NO 172
<211> LENGTH: 13
<212> TYPE: PRT
<213> ORGANISM: Artificial Sequence
<220> FEATURE:
<223> OTHER INFORMATION: amino acid linker

<400> SEQUENCE: 172

Ala Ser Thr Lys Gly Pro Ser Val Phe Pro Leu Ala Pro
1               5                   10

<210> SEQ ID NO 173
<211> LENGTH: 15
<212> TYPE: PRT
<213> ORGANISM: Artificial Sequence
<220> FEATURE:
<223> OTHER INFORMATION: amino acid linker

<400> SEQUENCE: 173

Gly Gly Gly Gly Ser Gly Gly Gly Gly Ser Gly Gly Gly Gly Ser
1               5                   10                  15
```

```
<210> SEQ ID NO 174
<211> LENGTH: 15
<212> TYPE: PRT
<213> ORGANISM: Artificial Sequence
<220> FEATURE:
<223> OTHER INFORMATION: amino acid linker

<400> SEQUENCE: 174

Gly Glu Asn Lys Val Glu Tyr Ala Pro Ala Leu Met Ala Leu Ser
1               5                  10                  15

<210> SEQ ID NO 175
<211> LENGTH: 15
<212> TYPE: PRT
<213> ORGANISM: Artificial Sequence
<220> FEATURE:
<223> OTHER INFORMATION: amino acid linker

<400> SEQUENCE: 175

Gly Pro Ala Lys Glu Leu Thr Pro Leu Lys Glu Ala Lys Val Ser
1               5                  10                  15

<210> SEQ ID NO 176
<211> LENGTH: 15
<212> TYPE: PRT
<213> ORGANISM: Artificial Sequence
<220> FEATURE:
<223> OTHER INFORMATION: amino acid linker

<400> SEQUENCE: 176

Gly His Glu Ala Ala Ala Val Met Gln Val Gln Tyr Pro Ala Ser
1               5                  10                  15

<210> SEQ ID NO 177
<211> LENGTH: 442
<212> TYPE: PRT
<213> ORGANISM: Homo sapiens

<400> SEQUENCE: 177

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Arg Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

165                 170                 175
Ser Gly Leu Tyr Ser Leu Ser Ser Val Val Thr Val Pro Ser Ser Asn
                180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
        210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 178
<211> LENGTH: 212
<212> TYPE: PRT
<213> ORGANISM: Homo sapiens

<400> SEQUENCE: 178

Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Trp Ser Ser Thr Pro Val
                85                  90                  95

-continued

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
        210

<210> SEQ ID NO 179
<211> LENGTH: 239
<212> TYPE: PRT
<213> ORGANISM: Artificial Sequence
<220> FEATURE:
<223> OTHER INFORMATION: protease-cleavable anti-TFPI scFv antibody

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Arg Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser Gly Gly Gly Ser Leu Val Pro Arg Gly Ser
        115                 120                 125

Gly Gly Gly Ser Ser Tyr Glu Leu Thr Gln Pro Pro Ser Val Ser
        130                 135                 140

Val Ser Pro Gly Gln Thr Ala Arg Ile Thr Cys Ser Gly Asp Asn Leu
145                 150                 155                 160

Pro Lys Tyr Tyr Ala His Trp Tyr Gln Gln Lys Pro Gly Gln Ala Pro
                165                 170                 175

Val Val Val Ile Phe Tyr Asp Val Asn Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Thr Gln Ala Met Asp Glu Ala Asp Tyr Tyr Cys Gln Ala Trp Trp
    210                 215                 220

Ser Ser Thr Pro Val Phe Gly Gly Gly Thr Lys Leu Thr Val Leu
225                 230                 235

```
<210> SEQ ID NO 180
<211> LENGTH: 717
<212> TYPE: DNA
<213> ORGANISM: Artificial Sequence
<220> FEATURE:
<223> OTHER INFORMATION: protease-cleavable anti-TFPI scFv antibody
      coding sequence

<400> SEQUENCE: 180
gaagttcagc tggtcgaaag tggtggcggt ctggttcaac cgggcggttc actgcgtctg      60
tcgtgcgcag caagcggttt taccttcagt tcctatggta tggattgggt ccgtcaggca     120
ccgggtaaag gtctggaatg ggtgtcatcg attcgtggca gccgcggttc tacctattac     180
gccgattcag ttaaaggccg ttttaccatc tctcgcgaca cagtaaaaa tacgctgtat     240 ctgcagatga acagcctgcg cgcggaagat accgccgtgt attactgtgc ccgtctgtat     300
cgctactggt tcgactactg gggccagggt acgctggtga ccgttagctc tggtggcggt     360
ggctctctgg ttccgcgtgg ctccggtggc ggtggctcat cctatgaact gacccaaccg     420
ccgagtgtct ccgtgtcacc gggtcagacg gcacgtatta cctgcagcgg tgataacctg     480
ccgaaatatt acgcgcattg gtatcagcaa aaaccgggcc aagccccggt ggttgtcatc     540 tttatgacg ttaatcgtcc gtccggtatc ccggaacgct ctcgggcag caactctggt     600 aatacggcaa ccctgacgat cagcggcacc caggcaatgg atgaagctga ctattactgt     660
caagcatggt ggagctctac gccggtgttt ggcggtggca cgaaactgac cgtgctg      717
```

THROMBIN/PLASMIN-REGULATED ANTIBODIES THAT BIND TFPI

This application claims the benefit of Ser. No. 61/617,837 filed on Mar. 30, 2012, which is incorporated herein by reference in its entirety.

All documents cited in this disclosure are incorporated herein by reference in their entireties.

This application incorporates by reference a 64 kb text file created on Mar. 26, 2012 and named "0297301274sequence-listing.txt," which is the sequence listing for this application.

TECHNICAL FIELD

The technical field is treatment of hemophilia and other coagulopathies.

DETAILED DESCRIPTION

Figure 1:
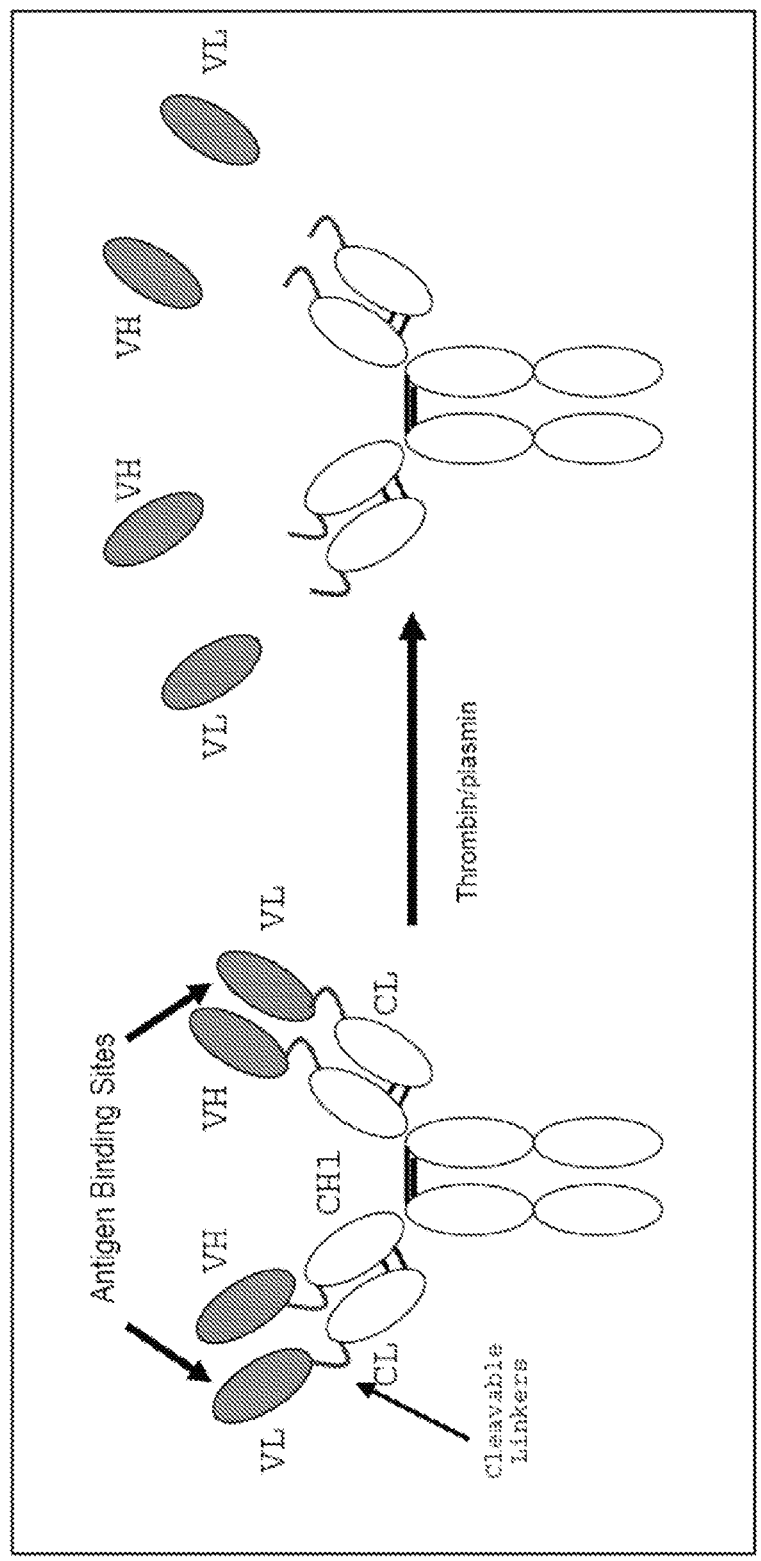
FIG. 1. Illustration of an embodiment of a protease-regulated antibody. VH, heavy chain variable region; VL, light chain variable region; CH, heavy chain constant region; CL, light chain constant region.

This disclosure provides protease-regulated antibodies which specifically bind to tissue factor pathway inhibitor (TFPI). The antibodies are useful for treating bleeding disorders such as hemophilia. In some embodiments, protease-regulated anti-TFPI antibodies can be cleaved by thrombin and/or plasmin. By initially inhibiting TFPI, such protease-regulated anti-TFPI antibodies promote the generation of thrombin and/or plasmin, which in turn cleaves the antibodies and removes or significantly reduces their binding activity to TFPI. This negative feedback allows the antibodies to promote coagulation within a safe therapeutic window.

1. Protease-Regulated Anti-TFPI Antibodies

Protease-regulated antibodies disclosed herein specifically bind to TFPI; i.e., they bind to TFPI with an affinity that is higher (e.g., at least two-fold higher) than their binding affinity for an irrelevant antigen (e.g., BSA, casein). The term "tissue factor pathway inhibitor" or "TFPI" as used herein refers to any variant, isoform and species homolog of human TFPI that is naturally expressed by cells.

In some embodiments, protease-regulated antibodies bind to TFPI with an affinity of at least about $10^5$ $M^{-1}$ to about $10^{12}$ $M^{-1}$ (e.g., $10^5$ $M^{-1}$, $10^{5.5}$ $M^{-1}$, $10^6$ $M^{-1}$, $10^{6.5}$ $M^{-1}$, $10^7$ $M^{-1}$, $10^{7.5}$ $M^{-1}$, $10^8$ $M^{-1}$, $10^{8.5}$ $M^{-1}$, $10^9$ $M^{-1}$, $10^{9.5}$ $M^{-1}$, $10^{10}$ $M^{-1}$, $10^{10.5}$ $M^{-1}$, $10^{11}$ $M^{-1}$, $10^{11.5}$ $M^{-1}$, $10^{12}$ $M^{-1}$.) The affinity ($K_d$) of antibody binding to an antigen can be assayed using any method known in the art including, for example, immunoassays such as enzyme-linked immununo-specific assay (ELISA), Bimolecular Interaction Analysis (BIA) (e.g., Sjolander & Urbaniczky; Anal. Chem. 63:2338-2345, 1991; Szabo, et al., Curr. Opin. Struct. Biol. 5:699-705, 1995), and fluorescence-activated cell sorting (FACS) for quantification of antibody binding to cells that express an antigen. BIA is a technology for analyzing biospecific interactions in real time, without labeling any of the interactants (e.g., BIACORE™). Changes in the optical phenomenon surface plasmon resonance (SPR) can be used as an indication of real-time reactions between biological molecules.

A protease-regulated anti-TFPI antibody can be constructed using a substantially full-length immunoglobulin molecule (e.g., IgG1, IgG2a, IgG2b, IgG3, IgG4, IgM, IgD, IgE, IgA), an antigen binding fragment thereof, such as a Fab or F(ab')$_2$, or a construct containing an antigen binding site, such as a scFv, Fv, or diabody, which is capable of specific binding to TFPI. The term "antibody" also includes other protein scaffolds that are able to orient antibody complementarity-determining region (CDR) inserts into the same active binding conformation as that found in natural antibodies such that the binding to TFPI observed with these chimeric proteins is maintained relative to the TFPI binding activity of the natural antibody from which the CDRs were derived.

An "isolated antibody" as used herein is an antibody which is substantially free of other antibodies having different antigenic specificities (e.g., an isolated antibody that binds to TFPI is substantially free of antibodies that bind antigens other than TFPI). An isolated antibody that binds to an epitope, isoform, or variant of human TFPI may, however, have cross-reactivity to other related antigens, e.g., from other species (e.g., TFPI species homologs). An isolated antibody can be substantially free of other cellular material and/or chemicals.

The protease-regulated antibodies disclosed herein are engineered to comprise a protease cleavage site recognized by one or more proteases. As used herein, "protease cleavage site" refers to an amino acid sequence that is recognized and cleaved by a protease. In some embodiments, the protease cleavage site is positioned between its variable and constant regions. In some embodiments, protease-regulated anti-TFPI antibodies include one or more protease cleavage sites that can be cleaved by thrombin, plasmin, and/or Factor Xa. In some embodiments, the amino acid sequence between the variable and constant regions of a protease-regulated anti-TFPI antibody comprises a polypeptide linker in addition to the protease cleavage site (as illustrated, for example, in FIG. 1). The linker can be a single amino acid or a polypeptide sequence (e.g., up to 100 amino acids). For example, the linker can be GGGGS (SEQ ID NO:149). Other useful linkers include those shown in SEQ ID NOS: 151-176. In other embodiments, no linker is present, and the cleavage site itself is inserted between the variable and constant regions.

At least two optimal cleavage sites for thrombin have been determined: (1) $X_1$-$X_2$—P—R—$X_3$-$X_4$ (SEQ ID NO:147), where $X_1$ and $X_2$ are hydrophobic amino acids and $X_3$ and $X_4$ are nonacidic amino acids; and (2) GRG. Thrombin specifically cleaves after the arginine residue. Plasmin can also cleave the two aforementioned cleavage sites, however with less specificity as compared to thrombin. Other useful thrombin cleavage sites are provided as SEQ ID NOS:1-60. Other useful plasmin cleavages sites are provided as SEQ ID NOS:12, 47, 48, 53, and 61-130. In some embodiments, the cleavage site is LVPRGS (SEQ ID NO:137).

In some embodiments, a Factor Xa cleavage site, such as I-(E or D)-G-R (SEQ ID NO:148), is used. Other useful Factor Xa cleavage sites are provided as SEQ ID NOS:29, 59, and 61-69. Other thrombin and FXa cleavage sites or sequences can be found from previous publication authored by Bianchini [Bianchini E P et al 2002 JBC]. One protease-regulated antibody may comprise more than one protease cleavage sites.

In addition to cleavage site, a second binding site of protease, so-called exosite, can be introduced into a protease-regulated TFPI antibody to make the cleavage more efficient. The exosite of thrombin can be from the native exosite of protease substrates or inibitor, such as PAR1, fibrinogen and hirudin. The exosite can also be a derivative of native exosite.

Protease-regulated TFPI antibodies can be produced synthetically or recombinantly. A number of technologies are available to produce antibodies. For example, phage-antibody technology can be used to generate antibodies (Knappik et al., *J. Mol. Biol.* 296:57-86, 2000). Another approach for obtaining antibodies is to screen a DNA library from B cells as described in WO 91/17271 and WO 92/01047. In these methods, libraries of phage are produced in which members display different antibodies on their outer surfaces. Antibodies are usually displayed as Fv or Fab fragments. Phage displaying antibodies are selected by affinity enrichment for binding to a selected protein. Antibodies can also be produced using trioma methodology (e.g., Oestberg et al., *Hybridoma* 2:361-367, 1983; U.S. Pat. No. 4,634,664; U.S. Pat. No. 4,634,666).

Antibodies can also be purified from any cell that expresses the antibodies, including host cells that have been transfected with antibody-encoding expression constructs. The host cells can be cultured under conditions whereby the antibodies are expressed. Purified antibody can be separated from other cellular components that can associate with the antibody in the cell, such as certain proteins, carbohydrates, or lipids, using methods well known in the art. Such methods include, but are not limited to, size exclusion chromatography, ammonium sulfate fractionation, ion exchange chromatography, affinity chromatography, and preparative gel electrophoresis. Purity of the preparations can be assessed by any means known in the art, such as SDS-polyacrylamide gel electrophoresis. A preparation of purified antibodies can contain more than one type of antibody.

Alternatively, protease-regulated anti-TFPI antibodies can be produced using chemical methods to synthesize its amino acid sequence, such as by direct peptide synthesis using solid-phase techniques (e.g., Merrifield, J. *Am. Chem. Soc.* 85:2149-2154, 1963; Roberge et al., *Science* 269:202-204, 1995). Protein synthesis can be performed using manual techniques or by automation. Optionally, fragments of antibodies can be separately synthesized and combined using chemical methods to produce a full-length molecule.

A protease-regulated anti-TFPI antibody can also be constructed in a "single chain Fv (scFv) format," in which a protease cleavage site is inserted in or around a peptide linker between the variable region of light chain and the variable region of heavy chain of a scFv. As the peptide linker is necessary to hold together the two variable regions of a scFv for antigen binding, cleavage of the peptide linker or flanking region allows a protease of interest to inactivate or to down-regulate the binding of scFv to its antigen. The amino acid sequence SEQ ID NO:179 (which can be encoded by SEQ ID NO:180) is an example of a protease-regulated anti-TFPI antibodies in scFv format.

In some embodiments, protease-regulated TFPI antibodies are constructed in "IgG format," having two binding sites, and can comprise one, two, three, or four protease cleavage sites on the heavy chain, light chain, or both. In each case, a protease cleavage site can be flanked on either or both sides by a linker. Further, in each case, the cleavage sites can be the same or different. "IgG-linker1" (Example 5) and "IgG-linker2" are examples of protease-regulated anti-TFPI antibodies in IgG format:

| | light chain | | heavy chain | |
|---|---|---|---|---|
| | amino acid | DNA | amino acid | DNA |
| IgG-linker1 | SEQ ID NO: 139 | SEQ ID NO: 141 | SEQ ID NO: 140 | SEQ ID NO: 142 |
| IgG-linker2 | SEQ ID NO: 143 | SEQ ID NO: 145 | SEQ ID NO: 144 | SEQ ID NO: 146 |

2. Negative Feedback

Protease-regulated antibodies can include a protease cleavage site of a protease upregulated or generated as a result of the function of the antibody. Such protease can then cleave the protease-regulated antibody thereby providing a negative feedback loop which can be useful in preventing excess activity of the protease-regulated antibody.

For example, protease-regulated anti-TFPI antibodies which can be cleaved by thrombin and/or plasmin can exhibit such a negative feedback effect. Such protease-regulated anti-TFPI antibodies promote the generation of thrombin and/or plasmin. Thrombin and plasmin will in turn cleave the protease-regulated anti-TFPI antibodies and remove or significantly reduce their binding activity to TFPI. This negative feedback allows the antibodies to promote coagulation within a safe therapeutic window.

3. Polynucleotides

This disclosure also provides polynucleotides encoding protease-regulated antibodies. These polynucleotides can be used, for example, to produce quantities of the antibodies for therapeutic use.

Antibody-encoding cDNA molecules can be made with standard molecular biology techniques, using mRNA as a template. Thereafter, cDNA molecules can be replicated using molecular biology techniques known in the art and disclosed in manuals such as Sambrook, et al., (Molecular Cloning: A Laboratory Manual, (Second Edition, Cold Spring Harbor Laboratory Press; Cold Spring Harbor, N.Y.; 1989) Vol. 1-3). An amplification technique, such as PCR, can be used to obtain additional copies of the polynucleotides. Alternatively, synthetic chemistry techniques can be used to synthesize polynucleotides encoding protease-regulated anti-TFPI antibodies.

To express a polynucleotide encoding an antibody, the polynucleotide can be inserted into an expression vector that contains the necessary elements for the transcription and translation of the inserted coding sequence. Methods that are well known to those skilled in the art can be used to construct expression vectors containing sequences encoding antibodies and appropriate transcriptional and translational control elements. These methods include in vitro recombinant DNA techniques, synthetic techniques, and in vivo genetic recombination. Such techniques are described, for example, in Sambrook, et al. (1989) and in Ausubel, et al., (Current Protocols in Molecular Biology, John Wiley & Sons, New York, N.Y., 1995).

A variety of expression vector/host systems can be utilized to contain and express sequences encoding antibodies. These include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV); or bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in strength and specificity. Depending on the vector system and host, any number of suitable transcription and translation elements, including constitutive and inducible promoters, can be used. For example, when cloning in bacterial systems, inducible promoters can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses can be used. If it is necessary to generate a cell line that contains multiple copies of a nucleotide sequence encoding an antibody, vectors based on SV40 or EBV can be used with an appropriate selectable marker.

General texts describing additional useful molecular biological techniques, including the preparation of antibodies, are Berger and Kimmel (Guide to Molecular Cloning Techniques, Methods in Enzymology, Vol. 152, Academic Press, Inc.); Sambrook, et al., (Molecular Cloning: A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, a joint venture between Green Publishing Associates, Inc. and John Wiley & Sons, Inc. (supplemented through 2000)); Harlow et al., (Monoclonal Antibodies: A Laboratory Manual, Cold Spring Harbor Laboratory Press (1988), Paul [Ed.]); Fundamental Immunology, (Lippincott Williams & Wilkins (1998)); and Harlow, et al. (Using Antibodies: A Laboratory Manual, Cold Spring Harbor Laboratory Press (1998)).

4. Pharmaceutical Compositions

A protease-regulated anti-TFPI antibody can be provided in a pharmaceutical composition comprising a pharmaceutically acceptable carrier. The pharmaceutically acceptable carrier preferably is non-pyrogenic. A pharmaceutical composition comprising a protease-regulated anti-TFPI antibody can be administered alone or in combination with at least one other agent, such as stabilizing compound, which can be administered in any sterile, biocompatible pharmaceutical carrier, including, but not limited to, saline, buffered saline, dextrose, and water. A variety of aqueous carriers can be employed, e.g., 0.4% saline, 0.3% glycine, and the like. These solutions are sterile and generally free of particulate matter. These solutions can be sterilized by conventional, well known sterilization techniques (e.g., filtration). The compositions can contain pharmaceutically acceptable auxiliary substances as required to approximate physiological conditions such as pH adjusting and buffering agents, etc. The concentration of protease-regulated anti-TFPI antibody in a pharmaceutical composition can vary widely, i.e., from less than about 0.5%, usually at or at least about 1% to as much as 15 or 20% by weight and will be selected primarily based on fluid volumes, viscosities, etc., according to the particular mode of administration selected. See U.S. Pat. No. 5,851,525. If desired, more than one different protease-regulated anti-TFPI antibody can be included in a pharmaceutical composition.

In addition to the active ingredients, pharmaceutical compositions can contain suitable pharmaceutically-acceptable carriers comprising excipients and auxiliaries that facilitate processing of the compositions into preparations which can be used pharmaceutically. Pharmaceutical compositions can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

After pharmaceutical compositions have been prepared, they can be placed in an appropriate container and labeled for treatment of an indicated condition. Such labeling would include amount, frequency, and method of administration.

5. Methods

Pharmaceutical compositions comprising one or more protease-regulated anti-TFPI antibodies can be administered to a patient alone, or in combination with other agents, drugs or coagulation factors, to treat hemophilia or other clotting disorders. A "therapeutically effective dose" of protease-regulated anti-TFPI antibody refers to that amount of protease-regulated anti-TFPI antibody that will promote coagulation or reduce bleeding time. The determination of a therapeutically effective dose is well within the capability of those skilled in the art.

A therapeutically effective dose can be estimated initially either in cell culture assays or in animal models, usually rats, mice, rabbits, dogs, or pigs. An animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population) of a protease-regulated anti-TFPI antibody can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. Data obtained from cell culture assays and animal studies are used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the patient who requires treatment. Dosage and administration are adjusted to provide sufficient levels of the protease-regulated TFPI antibody or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

In some embodiments, therapeutically effective in vivo dosages of a protease-regulated anti-TFPI antibody are in the range of about 5 μg to about 100 mg/kg, about 1 mg to about 50 mg/kg, about 10 mg to about 50 mg/kg of patient body weight.

The mode of administration of a pharmaceutical composition comprising a protease-regulated anti-TFPI antibody can be any suitable route which delivers the antibody to the host (e.g., subcutaneous, intramuscular, intravenous, or intranasal administration).

In some embodiments, a protease-regulated anti-TFPI antibody is administered without other therapeutic agents. In some embodiments, a protease-regulated anti-TFPI antibody is administered in combination with other agents, such as drugs or coagulation factors, to enhance initial production of thrombin while ensuring that the thrombin level stays below the range that may cause thrombosis in some people with coagulopathy. The administration of the protease-regulated anti-TFPI antibody can be before, after, or at substantially the same time as the administration of other agents.

Nothing in this specification should be considered as limiting the scope of this disclosure. All examples presented are representative and non-limiting. The above-described embodiments can be modified or varied, as appreciated by those skilled in the art in light of the above teachings. It is therefore to be understood that, within the scope of the claims and their equivalents, the embodiments disclosed herein can be practiced otherwise than as specifically described.

Example 1

Construction of Protease-Regulated Anti-TFPI Fab Fragments

Two protease-regulated anti-TFPI Fabs, "Fab-1" and "Fab-2," were based on the anti-TFPI antibody sequences shown in SEQ ID NO:177 (heavy chain) and SEQ ID NO:178 (light chain). Both Fabs have the thrombin/plasmin protease cleavage site, LVPRGS (SEQ ID NO:137) inserted C-terminal to both variable domains. The cleavage site in Fab-1 is flanked by a (Gly)$_4$Ser linker. Fab-2 contains the six amino acid cleavage site alone, no linker is present. Thrombin and plasmin will cleave C-terminal to the Arg (R) residue of LVPRGS (SEQ ID NO:137). DNA encoding the Fabs was synthesized by GenScript with optimized codons for bacterial expression. The amino acid and DNA sequences for the Fabs are identified in the table below.

| | |
|---|---|
| Fab-1 variable and constant light amino acid sequence | SEQ ID NO: 131 |
| Fab-1 variable and constant heavy amino acid sequence | SEQ ID NO: 133 |
| Fab-1 DNA Sequence | SEQ ID NO: 134 |
| Fab-2 variable and constant light amino acid sequence | SEQ ID NO: 135 |
| Fab-2 variable and constant heavy amino acid sequence | SEQ ID NO: 136 |
| Fab-2 DNA Sequence | SEQ ID NO: 138 |

The Fab coding regions were digested with the restriction enzymes BsaI and HindIII (New England Biolabs). The DNA fragments were purified using an agarose gel and subcloned into pBADmycHisA (Invitrogen). The cloned DNA was ligated and transformed using standard techniques. Positive clones were confirmed by DNA sequencing and used for BL21 *E. coli* expression.

Example 2

Western Blot of Thrombin-Cleaved Fabs

Approximately 2.5 μg of the crudely purified Fab-1 and Fab-2 were digested with 0, 2 or 10 units of thrombin (Novagen) for 1 hr at 37° C. Digests were run on a 4-15% CRITEREON™ TGX™ gel (Bio-Rad). Protein were transferred to a nitrocellulose membrane and probed with an anti-human Fab antibody (Southern Biotech).

Figure 2:
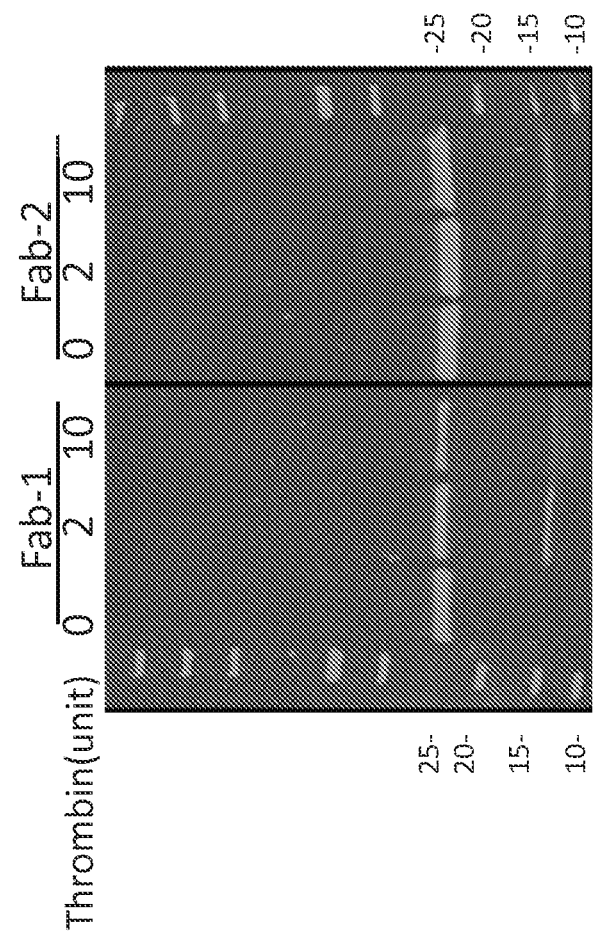
FIG. 2. Western blot of two protease-regulated anti-TFPI Fab fragments ("Fab-1" and "Fab-2"), with and without thrombin digestion.

The Western blot of Fab-1 and Fab-2 cleavage is shown in FIG. 2. All samples were reduced. Bands at approximately 12 kDA were observed for both Fabs when treated with thrombin. These bands were not present in the samples without thrombin digestion, indicating that the small size protein was the product of thrombin cleavage.

Example 3

TFPI ELISA of Thrombin Digested Fab-1 and Fab-2

Approximately 2.5 μg of partially purified Fab-1 and Fab-2 were digested with 2 units of biotinylated thrombin (Novagen) at 23° C. overnight. Streptavidin sepharose beads (100 μL) were added to the digestion to deplete the thrombin. The digested Fab samples were applied to a column that captures the sepharose bead/thrombin complex. The eluate contained the digested Fabs.

Figure 3:
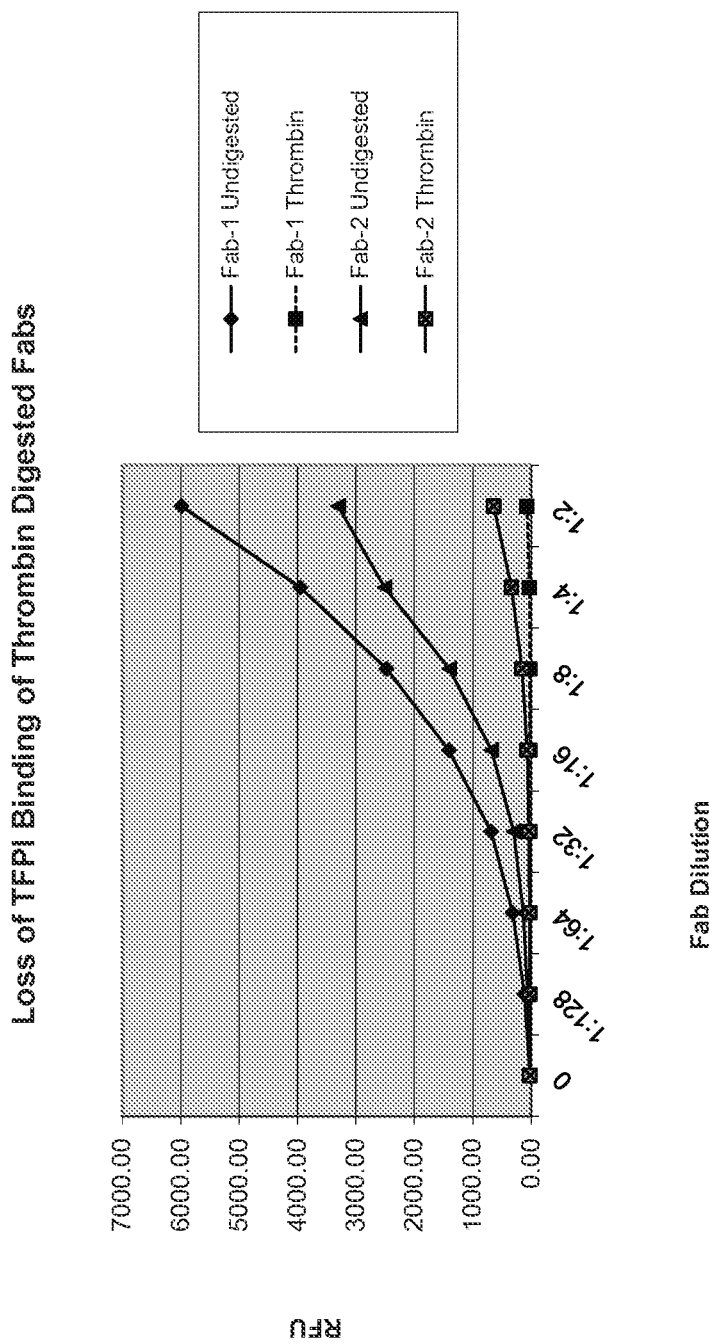
FIG. 3. Graph showing tissue factor pathway inhibitor (TFPI) binding of Fab-1 and Fab-2, with and without thrombin digestion, assayed by ELISA.

A MAXISORP® 96-well plate (Nunc) was coated with 1 μg/mL of TFPI in PBS overnight at 4° C. The plate was blocked for 1 hr at room temperature (RT) in 5% non-fat dry milk PBS/0.5% TWEEN-20® (PBS-T). Serial two-fold dilutions of undigested and digested Fab-1 and Fab-2 were added to the wells (100 μL/well) and incubated for 1 hr at RT. The plates were washed five times with PBS-T. A secondary HRP-conjugated anti-Fab antibody was added (100 μL of a 1:10,000 dilution) for detection with an AMPLEX® Red (Invitrogen) solution. As shown in FIG. 3, thrombin digestion significantly reduced the signal of TFPI binding.

Example 4

BIACORE™ Measurements of Thrombin-Digested Fab-1 and Fab-2

Approximately 2.5 μg of crudely purified Fab-1 and Fab-2 were digested with 2 units of biotinylated thrombin (Novagen) at 23° C. overnight. Streptavidin sepharose beads (100 μL) were added to the digestion to deplete the thrombin. The digested Fab samples were applied to a column that captures the sepharose bead/thrombin complex. The eluate contained the digested Fabs.

For BIACORE™ analysis, human TFPI (American Diagnostica) was immobilized using amine coupling at targeted level of 100 relative units (RU), and the antibodies were injected in the mobile phase. HBS-p was used as the running buffer. A reference channel was prepared using blank immobilization where the surface was activated and then inactivated without any immobilized protein. A manual run was performed to measure elevated RU of the Fabs and a buffer control.

Figure 4:
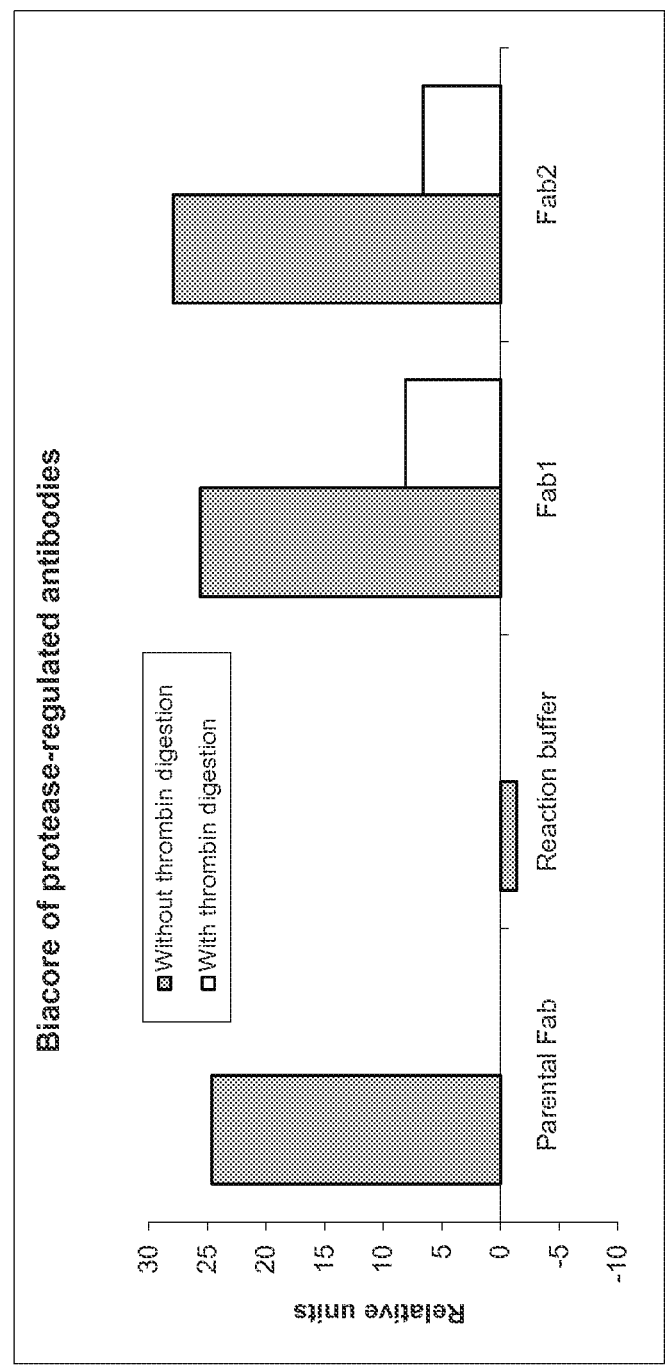
FIG. 4. Graph showing BIACORE™ measurement of TFPI binding of Fab-1 (Fab1) and Fab-2 (Fab2) with and without thrombin digestion.

As shown in FIG. 4, The parental Fab without cleavable linker generated 24.6 RU, comparable to undigested Fab-1 (25.6 RU) and Fab2 (27.9 RU). After thrombin cleavage, the binding signal of Fab-1 and Fab-2 was reduced by more than 50%, indicating that cleaved Fab-1 and Fab-2 not only lost the constant domain, but also lost binding activity to TFPI.

Example 5

IgG Expression and Purification

A protease-regulated anti-TFPI immunoglobulin molecules, "IgG-linker1," was constructed based on parental anti-TFPI antibody sequences shown in SEQ ID NO:177 (heavy chain) and SEQ ID NO:178 (light chain). To facilitate molecular cloning, a BlpI site was introduced in the heavy chain coding sequence. Compared to the position of protease cleavable linker in Fab-1, the introduction of BlpI site shifts the linker position of IgG-linker1 two amino acids to the constant region.

Figure 5:
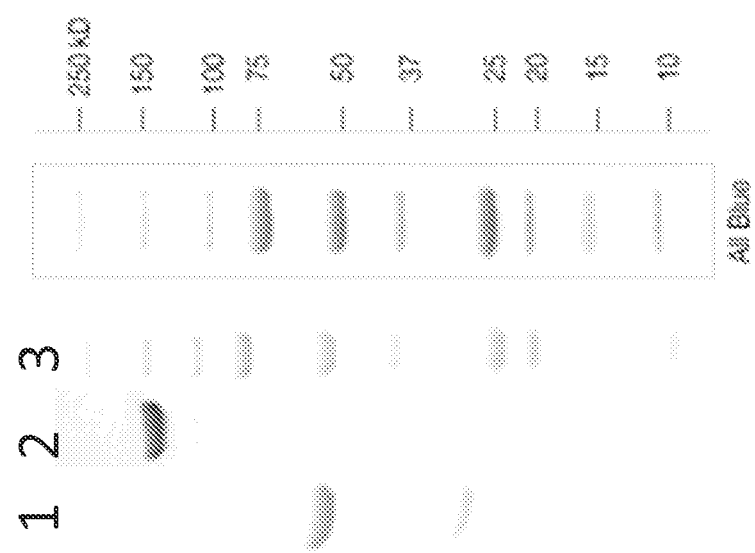
FIG. 5. SDS-PAGE of purified IgG antibody expressed in HEK293 6E cells.

HEK293 6E cells were transfected with constructed IgG expression vectors, and the culture supernatant containing the IgG antibodies was harvested. The antibodies were purified using an affinity column of MABSELECT SURE™ followed by SUPERDEX™ 200 chromatography. The purified IgG-linker1 on SDS-PAGE is shown FIG. 5.

Example 6

Western Blot of Parental IgG and IgG-Linker1

Figure 6:
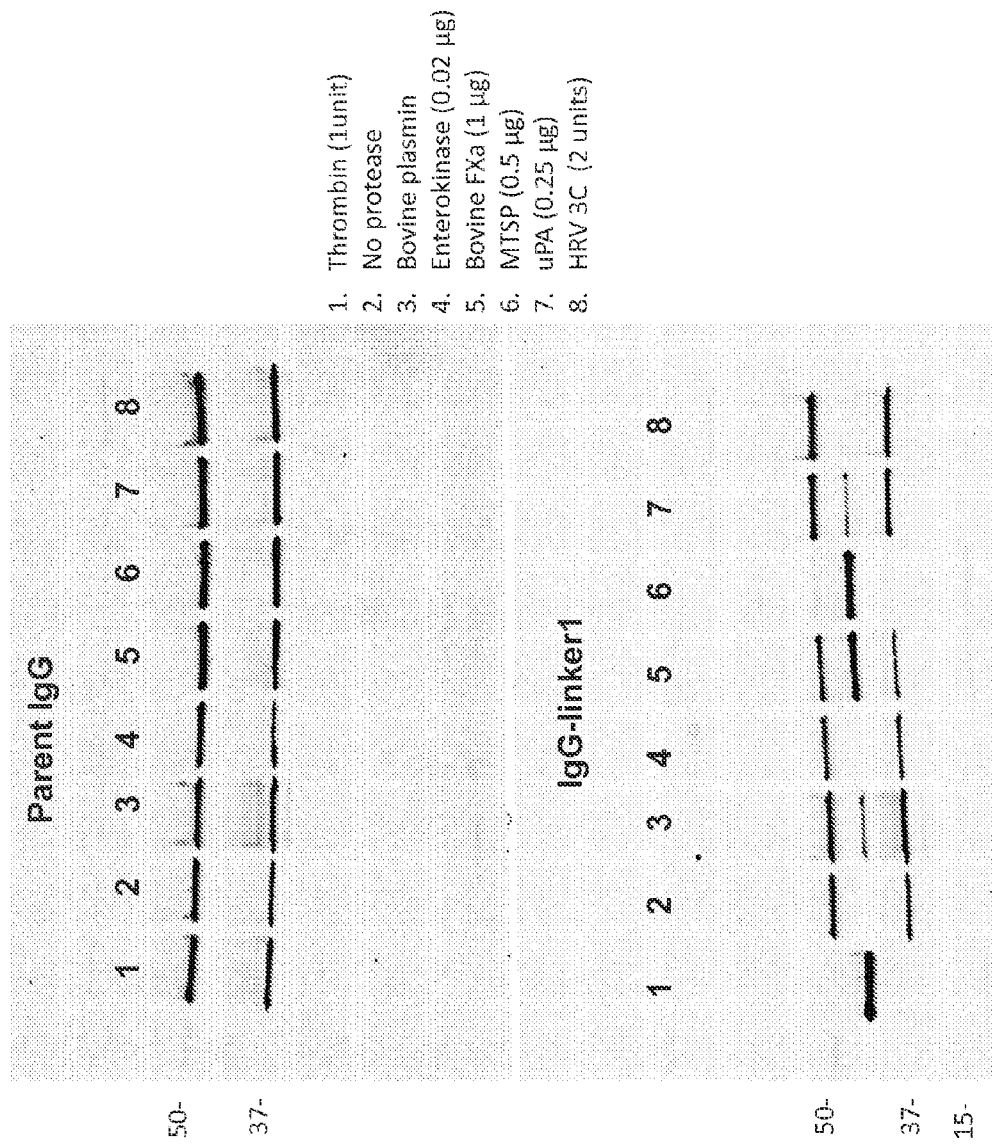
FIG. 6. Western Blot of parental IgG ("Parent IgG;" top) and IgG2-linker1 (bottom). Lane 1, digestion with thrombin (1 unit); lane 2, no protease (control); lane 3, digestion with bovine plasmin; lane 4, digestion with enterokinase (0.02 µg); lane 5, digestion with bovine Factor Xa (1 µg); lane 6, digestion with matriptase (MTSP) (0.5 µg); lane 7, digestion with urokinase (uPA) (0.25 µg); lane 8, digestion with human rhinovirus 3C protease (HRV 3C) (2 units).

Purified parental IgG and IgG-linker1 (0.5 µg) were digested with thrombin, bovine plasmin, bovine Factor Xa, matriptase (MTSP), urokinase (uPA), or human rhinovirus 3C protease (HRV 3C). The antibodies were incubated with the proteases for 1 hr at 37° C. Digests were run on a 4-20% CRITEREON™ TGX™ gel (Bio-Rad). Protein was transferred to a nitrocellulose membrane and probed with an anti-human IgG heavy and light chain antibody (Pierce). Western blots of IgG2 and IgG2-linker1 are shown in FIG. 6. All samples were reduced.

Intact IgG produced two bands under reducing conditions. The two bands correspond to the heavy chain (50 kD) and the light chain (25 kD). Digested antibody IgG-linker1 showed a shift in molecular weight vs. undigested antibody. The following proteases were used to digests the antibodies: thrombin, plasmin, bovine Factor Xa, MTSP, and uPA. The digested IgG-linker1 antibody showed a shift in the molecular weight of the heavy chain from 50 kD to 37 kD. This size shift correlates with the loss of the VH domain from the heavy chain. There was also a molecular weight shift of the 25 kD light chain to a faint band around 16 kDa, which indicates cleavage of the VL domain from the light chain. The proteases did not cleave parental IgG, indicating that molecular weight loss was a result of the protease digestion due to the cleavage site engineered into the antibody.

Example 7

TFPI-Binding ELISA of Thrombin Digested Parental IgG and IgG-Linker1

One microgram of the full length antibodies, parental IgG and IgG-linker1, were digested with 1 unit of biotinylated thrombin (Novagen) for 1 hr at 37° C. Then 50 µL of streptavidin sepharose beads were added to the digestion to deplete the thrombin. The digested IgG samples were applied to a column that captures the sepharose bead/thrombin complex. The eluate contains the digested IgGs.

A MAXISORP® 96-well plate (Nunc) was coated with 1 µg/mL of TFPI in PBS over night at 4° C. The plate was blocked for 1 hr at room temperature (RT) in 5% non-fat dry milk PBS/0.5% TWEEN® 20 (PBS-T). Serial two-fold dilutions of undigested and digested parental IgG and IgG-linker1 were added to the wells (100 µL/well) and incubated for 1 hr at RT. The plate was washed five times in PBS-T. A secondary HRP conjugated anti-Fab-antibody was added (100 µL of a 1:10,000 dilution) for detection with an AMPLEX RED® (Invitrogen) solution.

Figure 7:
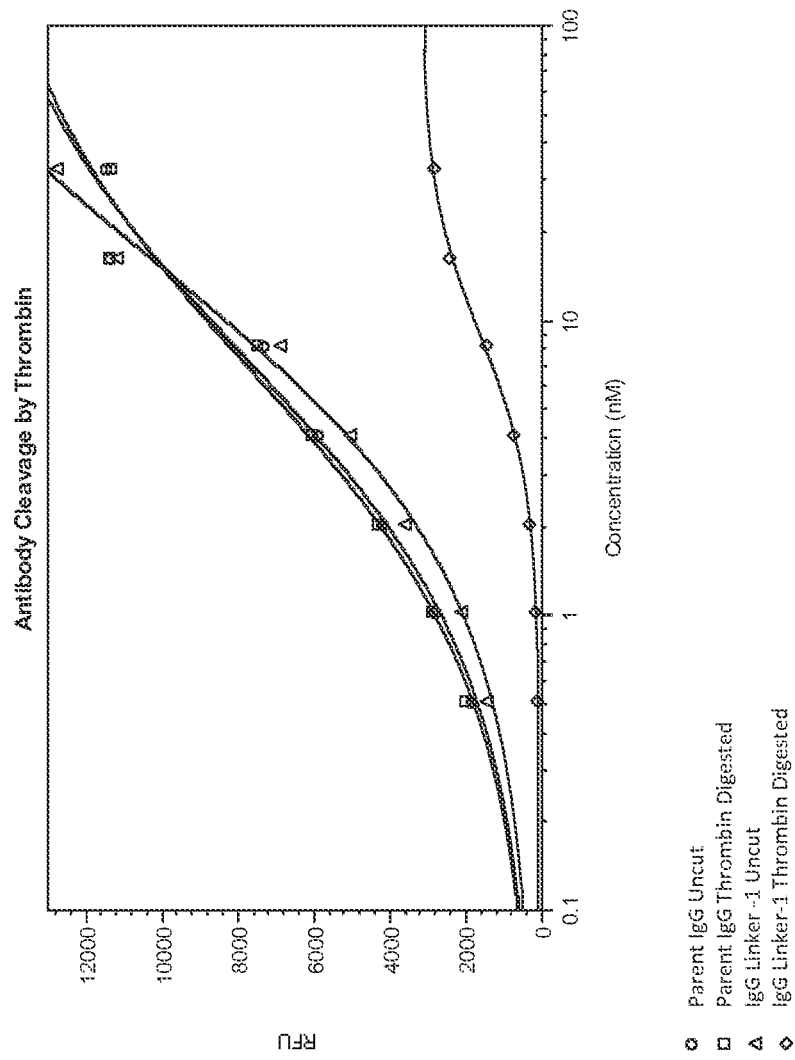
FIG. 7. Graph showing TFPI binding of IgG with and without thrombin digestion, assayed by ELISA.

The results of the TFPI binding ELISA are shown in FIG. 7. Loss of TFPI binding by thrombin digested IgG Linker-1 is shown. The TFPI binding of undigested IgG-linked was similar to the TFPI binding of the undigested and thrombin-digested parental IgG.

Example 8

BIACORE™ Analysis of Parental IgG and IgG-Linker1

A CM4 sensor chip was immobilized with a low density of human TFPI using an amine coupling kit (GE Health-Care). Kinetic assays of parental IgG and IgG-linker1 were conducted using different concentration of the antibodies, followed by regeneration with pH 1.5 glycine buffer. The parental IgG and IgG-linked antibodies at a concentration of 1 µg were digested with 1 unit of biotinylated thrombin (Novagen) for 1 hr at 37° C. The antibodies with or without digestion were injected to a BIACORE™ system for TFPI-binding analysis. The following figure shows the signal generated from injection 45 µl of 6.25 µg/ml antibodies or control samples.

In kinetics assay, parental IgG and IgG2-linker1 have association rates (ka) of $1.536 \times 10^6$/Ms and $1.902 \times 10^6$/Ms, respectively. The two antibodies did not have measurable dissociation in 30 minutes. This indicates that the insertion of linked did not significantly change binding activity of the antibody.

Figure 8:
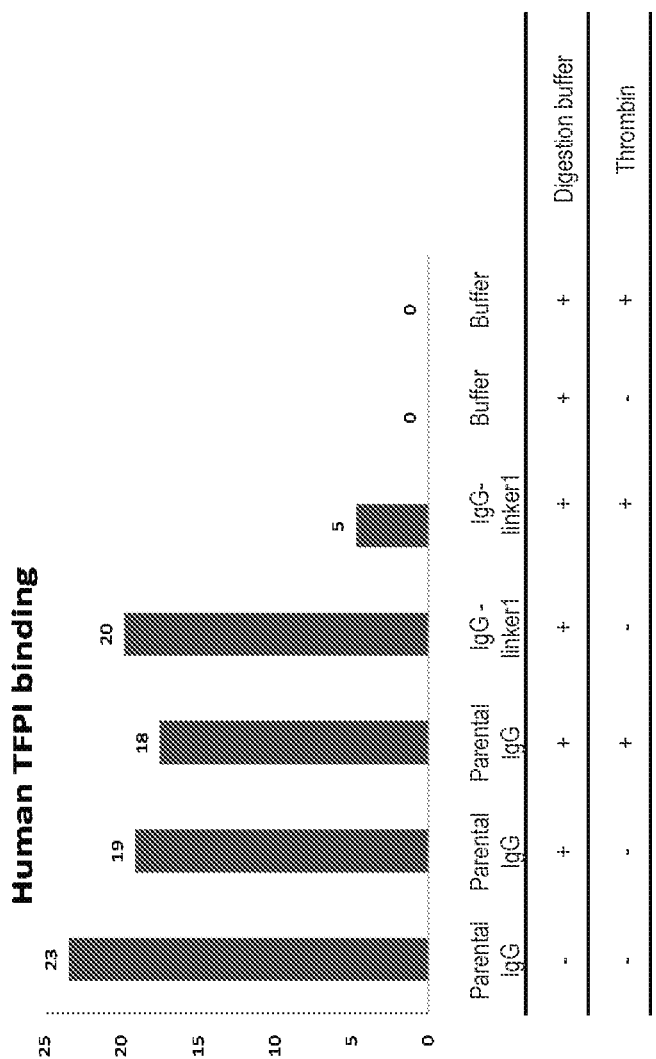
FIG. 8. Graph showing BIACORE™ measurement of TFPI binding of parental IgG and IgG-linker1, with and without thrombin digestion.

The effect of thrombin cleavage on the antibodies is shown in FIG. 8. Thrombin digestion slightly decreased the parental IgG binding on TFPI, whereas thrombin digestion reduced IgG2-linker1 binding on TFPI from 20 RU to 5 RU, a 75% decrease.

Example 9

Western Blot of Protease/Coagulation Factor Treated IgG-Linker1 and Parental IgG The following human proteases/coagulation factors were used to digest 80 nM of IgG-Linker 1 and the WT antibody:

thrombin (0.1 µM), plasmin (0.1 µM), Factor VIIa (0.01 µM), Factor IXa (0.089 µM), Factor Xa (1304), Factor XIa (0.03104), Factor XIIIa (0.03 µM). The treated material was run on a 4-15% CRITEREON™ TGX gel (Bio-Rad). Proteins were transferred to a nitrocellulose membrane and probed with an anti-human IgG antibody (Pierce).

Figure 9:
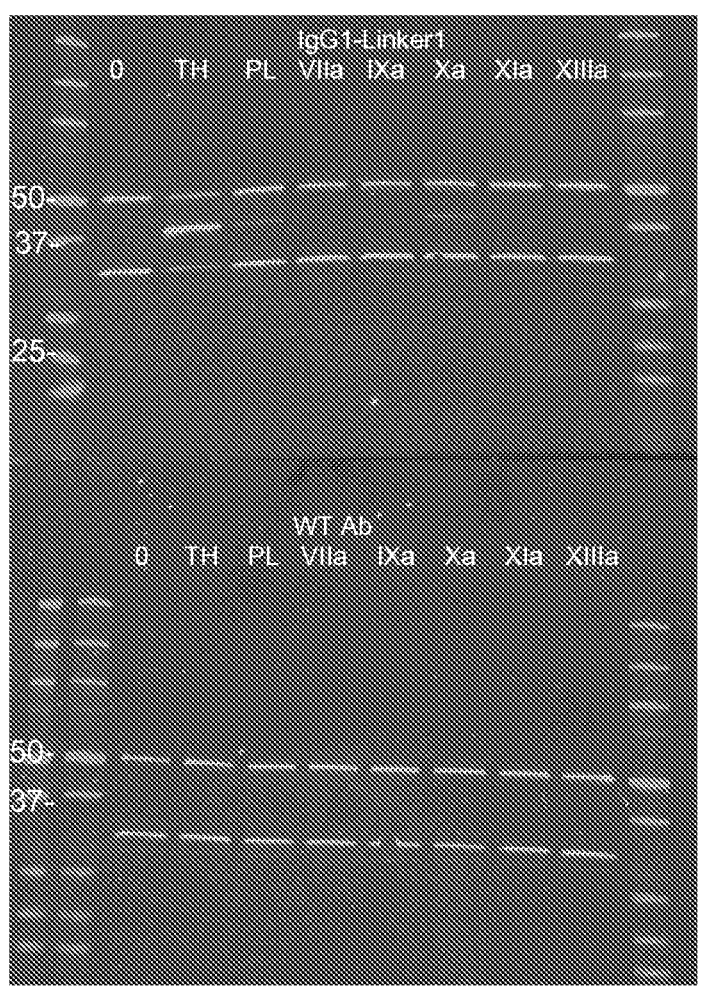
FIG. 9. Western blot, showing protease digestion of IgG-Linker1 and WT antibody with human proteases.

Human thrombin, plasmin and FactorXa digested IgG-Linker1, thrombin digesting most efficiently (FIG. 9) as shown by the appearance of a 37 kDa band. The proteases did not cleave the parental IgG, indicating that molecular weight loss was a result of the protease digestion due to the cleavage site engineered into the antibody.

The invention claimed is:

1. A protease-regulated antibody which specifically binds to tissue factor pathway inhibitor (TFPI), comprising:

(a) the amino acid sequence of SEQ ID NO: 131 which comprises the variable light domain and constant light domain of the protease-regulated antibody and the protease cleavage site of SEQ ID NO: 137; and (b) the amino acid sequence of SEQ ID NO: 133 which comprises the variable heavy domain and constant heavy domain of the protease-regulated antibody and the protease cleavage site of SEQ ID NO: 137, wherein the protease-regulated antibody binds TFPI and promotes the generation of thrombin or plasmin.

* * * * *